United States Patent [19]

Buhr

[11] Patent Number: 5,486,603
[45] Date of Patent: Jan. 23, 1996

[54] OLIGONUCLEOTIDE HAVING ENHANCED BINDING AFFINITY

[75] Inventor: Chris A. Buhr, Daly City, Calif.

[73] Assignee: Gilead Sciences, Inc., Foster City, Calif.

[21] Appl. No.: 902,538

[22] Filed: Jun. 22, 1992

Related U.S. Application Data

[63] Continuation of Ser. No. 461,884, Jan. 8, 1990, abandoned.

[51] Int. Cl.$^6$ .......................... C07H 15/12; C07H 17/00; C07J 41/00; C07J 31/00

[52] U.S. Cl. .................... 536/24.3; 536/23.1; 536/24.5; 552/506; 552/515; 552/544; 552/557; 552/586; 552/588; 552/574; 552/604; 552/607; 552/625; 552/638

[58] Field of Search .................... 536/23.1, 24.3, 536/24.5; 552/515, 506, 544, 557, 586, 574, 607, 625, 609, 588, 638

[56] References Cited

U.S. PATENT DOCUMENTS 4,801,540  1/1989  Hiatt et al. ............................ 435/240.4

OTHER PUBLICATIONS

Letsinger et al. (1989) Proc. Natl. Acad. Sci., vol. 86, pp. 6553–6556.
Uhlman et al. (1990) Chemical Reviews, vol. 90, No. 4, pp. 555–582.
Chemical Abstracts (1988) vol. 109, No. 25, Abst. No. 225156z, Bichenkou et al. (1988).
Biol. Membranes, vol. 5, No. 7, pp. 735–737.
Asseline et al. J. Biol. Chem. 260:8936–8941, 1985.
Stein, et al., Cancer Research, 48:2659–2668, 1988.
Chen et al., J. Am. Chem. Soc., 110:6570–6572, 1988.
Telser, et al., J. Am. Chem. Soc. 111:7226–7232, 1989.
Telser, et al., J. Amer. Chem. Soc., 111:7221–7226, 1989.
Telser, et al., J. Am. Chem. Soc. 111:6966–6976, 1989.
Hui, et al., Nucl. Acid. Res. 17:4177–4187, 1989.
Maher, et al., Science 245:725–730, 1989.
Griffin, et al., Science 245:967–971, 1989.
Smith, et al., Proc. Natl. Acad. Sci. USA 83:2787–2791, 1986.
Agris, et al., Biochemistry, 25:6268–6275, 1986.
Gautier, et al., Nucl. Acids. Res. 15:6225–6641, 1987.
Milligan et al., Nucl. Acid. Res. 15:8783–8788, 1987.
Moser, et al., Science 238:645–650, 1987.
Van der Krol, et al., Biotechniques 6:958–978, 1988.
Sarin et al., Proc. Natl. Acad. Sci. USA, 85:7448–7451, 1988.
Wickstrom, et al., Proc. Natl. Acad. Sci., 85:1028–1032, 1988.

(List continued on next page.)

*Primary Examiner*—Mindy B. Fleisher

[57] ABSTRACT

The present invention relates to an oligonucleotide or analog thereof conjugated to a molecule comprising a structure, which structure (a) is of substantially fixed conformation; (b) contains, is directly attached to, or is attached to a carbon atom that is directly attached to, an first amine; and (c) contains, is directly attached to, or is attached to an atom that is directly attached to a phosphate, a second amine, or a cationic sulfur. In a preferred embodiment, the structure consists of at least a nonaromatic cyclic portion or substituted derivative thereof. In a specific embodiment, the structure is a nonaromatic cyclic compound. In another embodiment, the molecule is a steroid. In yet another particular aspect, the structure is an aromatic compound. In another embodiment, the structure can bind to a nucleic acid sequence in a nonintercalative manner. The invention also relates to a conjugate comprising a steroid or substituted derivative thereof containing, or attached directly or through a carbon atom to, an amine, which steroid or substituted derivative is conjugated to at least one hydrogen-phosphonate and a cation; such a conjugate may be used as an intermediate in synthesis. The oligonucleotide conjugates of the invention can have a number of uses. For example, the conjugates may be used for diagnostic purposes by detecting a nucleic acid sequence.

32 Claims, 21 Drawing Sheets

Oligo = 5'-TCT-CCC-TCT-CTT-TT-3'

OTHER PUBLICATIONS

Goodchild et al., Proc. Natl. Acad. Sci. USA 85:5507–5511 1988.
Cooney, et al., Science 241:456–459, 1988.
Letsinger, et al., J. Am. Chem. Soc. 110:4470–4471, 1988.
Zon, Pharm. Res. 5:539–549, 1988.
Chien, et al., J. Org. Chem. 29:315–318, 1964.
Mahler, et al., Biochemistry 7:1568–1582, 1968.
Waring, et al., Nucl. Acid Res. 2:567–586, 1975.
Saucier, et al., Biochem. 16:5879–5889, 1977.
Dattagupta, et al., Proc. Natl. Acad. Sci. U.S.A. 75:4286–4290, 1979.
Curphey, J. Org. Chem. 44:2805–2807, 1979.
Patel, et al., Proc. Natl. Acad. Sci. U.S.A. 78:4063–4067, 1981.
Letsinger, et al., J. Am. Chem. Soc. 103:7394, 1981.
Froehler, Tetrahedron Lett. 27:5575–5578, 1982.
Kawasaki, et al., Nucl. Acad. Res., 13:4991–5004, 1985.
Gourevitch, et al., Int. J. Biol. Macromol. 8:97–104, 1986.
Froehler, et al., Nucl. Acids Res. 14:5399–5407, 1986.

Oligo = 5'-TCT-CCC-TCT-CTT-TT-3'

4.

5.

6.

Oligo = 5'-TCT-CCC-TCT-CTT-TT-3'

17β-Hydroxy-5α-Androstan-3-One

NaCNBH₃ | NH₄OAc

3β-Amino-17β-Hydroxy-5α-Androstane $CF_3COEt$
Ethyltrifluoroacetate

17β-Hydroxy-3β-N-Trifluoroacylamino-5α-Androstane (1) P(triazole)$_3$
(2) TEAB

3β-N-Trifluoroacylamino-5α-Androstan-17β-O-yl-
Hydrogen-Phosphonate Triethylammonium Salt (1a)

3β-Hydroxy-5α-Androstan-17-One

↓ HClH₂NOH

3β-Hydroxy-5α-Androstan-17-Oxime

↓ H₂ | Cat.

17β-Amino-3β-Hydroxy-5α-Androstane

17β-N-Trifluorocylamino-3β-Hydroxy-5α-Androstane (1) P(triazole)₃
(2) TEAB

17β-N-Trifluoroacylamino-5α-Androstan-3β-O-yl-
Hydrogen-Phosphonate Triethylammonium Salt (2a)

3β-Hydroxy-5α-Pregnan-20-One

HClH₂NOH

3β-Hydroxy-5α-Pregnan-20-Oxime

Pt(IV) oxide
H₂

20-Amino-3β-Hydroxy-5α-Pregnane

20-N-Trifluoroacylamino-3β-Hydroxy-5α-Pregnane (1) P(triazole)₃
(2) TEAB

20-N-Trifluoroacylamino-5α-Pregnan-3β-O-yl-
Hydrogen-Phosphonate Triethylammonium Salt (3a)

17β-Hydroxy-5α-Androstan-3-One

3β-[N-(2-Aminoethyl)-Amino]-17β-Hydroxy-5α-Androstane

3β-[N-(2-N-Trifluoroacylaminoethyl)-N-Trifluoroacylamino]
-17β-Hydroxy-5α-Androstane (1) P(triazole)$_3$
(2) TEAB 3β-[N-(2-N-Trifluoroacylaminoethyl)-N-Trifluoroacylamino]-5α-Androstan-
3β-O-yl-Hydrogen-Phosphonate Triethylammonium Salt (4a)

5α-Pregnane-3,20-Dione

↓ HOAc
  MeOH
  NaCNBH₃      H₂N⁓⁓⁓OH 5-(20-Keto-5α-Pregnan-3β-N-yl)-Aminopentan-1-ol ↓ HClH₂NOH 5-(20-Oximo-5α-Pregnan-3β-N-yl)-Aminopentan-1-ol 5-(20-Amino-5α-Pregnan-3β-N-yl)-Aminopentan-1-ol 5-N-Trifluoroacyl-5-(20-N-Trifluoroacylamino-5α-Pregnan-3β-N-yl)-Aminopentan-1-ol 5-N-Trifluoroacyl-5-(20-N-Trifluoroacylamino-5α-Pregnan-3β-N-yl)-Aminopentan-1-O-yl-Hydrogen-Phosphonate Triethylammonium Salt (5a)

5α-Androstane-3,17-Dione 5-(17-Keta-5α-Androstan-3β-N-yl)-Aminopentan-1-ol

5-N-Trifluoroacyl-5-(17-Keta-5α-Androstan-3β-N-yl)-
Aminopentan-1-yl-Trifluoroacetate HClH₂NOH 5-N-Trifluoroacyl-5-(17-Oximo-5α-Androstan-3β-N-yl)-
Aminopentan-1-ol Pt(IV)oxide | H₂

5-N-Trifluoroacyl-5-(17β-N-Trifluoroacylamino-
5α-Androstan-3β-N-yl)-Aminopentan-1-O-yl-
Hydrogen-Phosphate Triethylammonium Salt (6a)

5-N-Trifluoroacyl-5-(17β-Amino-
5α-Androstan-3β-N-yl)-Aminopentan-1-ol

↓ Ethyltrifluoroacetate

5-N-Trifluoroacyl-5-(17β-N-Trifluoroacylamino-
5α-Androstan-3β-N-yl)-Aminopentan-1-ol (1) P(triazole)$_3$
(2) TEAB

↓

OLIGONUCLEOTIDE HAVING ENHANCED BINDING AFFINITY

This is a continuation of application Ser. No. 07/461,884, filed Jan. 8, 1990, now abandoned.

1. FIELD OF THE INVENTION

The invention is directed to an oligonucleotide or analog thereof conjugated to a molecule comprising a structure, which structure is of substantially fixed conformation, contains or is directly or indirectly attached to an amine, and contains or is directly or indirectly attached to a phosphate, a second amine, or a cationic sulfur. Such conjugates have a number of uses. For example, the conjugates may be used for diagnostic purposes by detecting a nucleic acid sequence.

2. BACKGROUND OF THE INVENTION

2.1. INTERACTION OF STEROID AMINES WITH OLIGONUCLEOTIDES

Steroid diamines have been found to exert a variety of effects in a number of biological systems. For example, these substances have been found to exert antimicrobial and mutagenic activity towards bacteriophages and interfere with the excitability of the neuromuscular junction in animals and man (reviewed in Waring and Henley, 1975, Nucl. Acids Res. 2: 567–586).

The interaction of steroid diamines in particular with DNA sequences has been widely studied. (See for example Hui et al., 1989, Nucl. Acids Res. 17: 4177–4187; Gourevitch and Puigdomenech, 1986, Int. J. Biol. Macromol. 8: 97–104; Patel et al., 1981, Proc. Natl. Acad. Sci. U.S.A. 78: 4063–4067; Dattagupta et al., 1978, Proc. Natl. Acad. Sci. U.S.A. 75: 4286–4290; and Warring and Henley, 1975, Nucl. Acids Res. 2: 567–586; and Mahler et al., 1968, Biochemistry 7: 1568–1582). Steroid diamines have been found to attach firmly to poly-anionic double-stranded DNA by electrostatic interactions (Saucier et al., 1978, Biochemistry 16: 5879). To date, no reports of binding of steroid amines to DNA-RNA complexes, RNA-RNA complexes, or oligonucleotide complexes including a triple helix structure have been found.

The steroid diamines consist of a rigid structure, the steroid. The two amines are affixed to the steroid at appropriate positions to allow for one of the amine groups to interact with one phosphate of the duplex, and the other amine group to interact with the second phosphate chain of the duplex via ionic bonds. The two amines and the rigid structure of the steroid diamines allows the steroid diamines to bind to nucleic acids duplexes in a different manner than the binding of such dicationic ligands as polymethylene diamines, e.g. putrescine, cadaverine. Firstly, steroid diamines show the usual rise of melting temperature (Tm) of DNA at a low steroid diamine/DNA ratio (input ratio) observed for other diamines, but the Tm's decrease at higher input ratios (Waring and Henley, 1975, Nucl. Acids Res. 2: 567–586). Secondly, steroid diamines have been found to have a hyperchromic effect and alter the optical rotatory dispersion and circular dichroism spectra of duplex DNA (Mahler et al., 1968, Biochemistry 7: 1568–1582). Thirdly, steroid diamines have been observed to cause the removal and reversal of the supercoiling in closed circular duplex DNA, attributable to the local unwinding of the DNA helix (Waring and Henley, 1975, Nucl. Acid Res. 2: 567–586). The results from extensive physicochemical studies appear to indicate that steroid amines bind to DNA in a nonintercalative manner and that binding of the steroid diamines induces a kink in the structure of DNA. The steroid diamine may partially insert between slightly unstacked base pairs, but does not intercalate. It was recently shown that the steroid diamine, dipyrandium binds preferentially to the minor groove of AT sequences. (Hui et al., 1989, Nucl. Acids Res. 17: 4177–4187).

The interaction of steroid monoamines bearing a single amino substituent at either the 3 or 17 position with circular DNA has also been studied (Waring and Henley, 1975, Nucl. Acids Res. 2: 567–586). It was found that the two 17β-aminoandrostane compounds tested had a positive effect on supercoiling. However, the effects of these monoamines on the Tm were observed to be considerably smaller than those of their diamine counterparts. The 3β-aminoandrostane compounds tested as well as the 17β-aminoandrostene compound were relatively ineffective. The monoamino steroids can only interact with one phosphate chain of a complex at a time, and so little or no stabilization of the complex is observed.

2.2. USE OF OLIGONUCLEOTIDES AS INHIBITORS OF THE EXPRESSION OF A NUCLEIC ACID

2.2.1. USE OF OLIGONUCLEOTIDES AS MODULATORS OF THE EXPRESSION OF A SINGLE-STRANDED NUCLEIC ACID

A large amount of research has been directed to the use of oligonucleotides as diagnostic tools. This work has been extensively reviewed (van der Krol et al., 1988, Biotechniques 6: 958–976; Stein and Cohen, 1988, Cancer Res. 48: 2659–2668; and Zon, 1988, Pharm. Res. 5: 539–549).

Another approach has involved conjugating the oligonucleotide to a molecule that will increase the efficiency of cell permeation by the oligonucleotide. Examples of such conjugates include cholesteryl-conjugated oligonucleotides (Letsinger et al., 1989, Proc. Natl. Acad. Sci. U.S.A. 86: 6553–6556) and a poly-L-lysine conjugate (Lemaitre et al., 1987, Proc. Natl. Acad. Sci. U.S.A. 84: 648–652). Another example includes an oligonucleotide joined through a linking arm to a group that imparts amphophilic character to the final product in order to increase the efficiency of cell permeation (PCT Publication No. WO 88/09810, published Dec. 15, 1988).

The interaction of nonrigid cationic oligonucleotides with complementary nucleic acid sequences has also been studied (Letsinger et al., 1988, J. Amer. Chem. Soc. 110: 4470–4471). Specifically, a morpholino group was conjugated to a phosphoramidite linkage via an ethyl group. The binding properties were found to be selectively influenced by changes in pH and the salt concentration.

Other investigators have studied the use of oligonucleotides linked to agents that are able to modify the target nucleic acid sequence. One such group of agents are intercalating agents which can bind to the duplex by internal insertion between adjacent base pairs. Examples of intercalators that have been attached to oligonucleotides and oligonucleotide analogs include acridine, anthridium, and photoactivatable psoralen (reviewed in Zon, 1988, Pharm. Res. 5: 539–549). Another such group of agents coupled to oligonucleotides include metal complexes such as EDTA-Fe(II), o-phenanthroline-Cu(I), or porphyrin-Fe(II) (reviewed in Krol et al., 1988, BioTechniques 6: 958–976).

These compounds can generate hydroxyl radicals in the presence of molecular oxygen and a reducing agent. The resulting radicals can cleave the complementary strand following attack on the target nucleic acid backbone. One problem with using such compounds is that since such oligonucleotides are reactive, they may be subject to autodegradation.

Letsinger (1981, J. Am. Chem. Soc. 103:7394) synthesized an dinucleotide derivative of phenanthridinium.

2.2.2. TRIPLE HELIX FORMATION

Another possible mechanism involves the hybridization of an oligonucleotide in a sequence specific manner to double stranded oligonucleotides resulting in the formation of a triple helix. Both purine oligodeoxyribonucleotides and pyrimidine oligodeoxyribonucleotides have been observed to bind to double stranded DNA (Griffin and Dervan, 1989, Science 245:967–971 and Cooney et al., 1988, Science 241:456) . Purine oligonucleotides have been postulated to bind parallel to purines in duplex DNA by triple helix formation.

Pyrimidine oligonucleotides have been shown to bind with sequence specific dependence to homopurine sites in duplex DNA (Moser and Dervan, 1987, Science 238: 634–650). These oligonucleotides bind in the major groove, parallel to the purine strand of Watson-Crick double-helical DNA. The binding affinity and specificity of the pyrimidine oligonucleotide for duplex DNA has been shown to be sensitive to pH, organic cosolvent, added cations, and temperature.

In one possible application, it has been suggested that the sequence specificity of homopyridine oligonucleotides would render such oligonucleotides useful as tools for mapping chromosomes when equipped with DNA cleaving moieties (Moser and Dervan, 1987, Science 238: 645–650). Micromolar concentrations of homopyrimidine oligodeoxyribonucleotides have also been shown to block recognition of double helical DNA by prokaryotic modifying enzymes and a eukaryotic transcription at a homopurine target site (Maher et al., 1989, Science 245: 725–730). Recently, results of a study of 20 base triplets indicate that the triple helix can be extended from homopurine to mixed sequences (Griffin and Dervan, 1989, Science 245: 967–971).

3. SUMMARY OF THE INVENTION

The invention is directed to an oligonucleotide or analog thereof conjugated to a molecule comprising a structure, which structure (a) is of substantially fixed conformation; (b) contains, is directly attached to, or is attached to a carbon atom that is directly atached to, a first amine; and (c) contains, is directly attached to, or is attached to an atom that is directly attached to, a phosphate, a second amine, or a cationic sulfur. Such structures shall be referred to herein as "rigid structures". In a preferred embodiment, the rigid structure consists of at least a nonaromatic cyclic compound or substituted derivative thereof. In specific embodiments, the rigid structure can be a nonaromatic cyclic compound, a steroid, an aromatic compound, or substituted derivatives thereof. The first and second amines can be the same or different. In one embodiment, the first amine is directly attached to the rigid structure. In another embodiment, the first amine is attached to a carbon that is directly attached to the rigid structure. In yet another embodiment, the first amine forms part of the rigid structure.

The invention further relates to a composition that may be used as a reaction intermediate in the synthesis of an oligonucleotide conjugate of the invention, in which the rigid structure is or is contained within a steroid or substituted derivative thereof. Such a composition comprises a steroid or substituted derivative thereof which (a) contains, is directly attached to, or is attached to a carbon atom that is directly attached to, an amine; and (b) is conjugated to at least one hydrogen-phosphonate and a cation. In a specific embodiment, the steroid is conjugated to the hydrogen-phosphonate through a linking chain. In a preferred embodiment, the oligonucleotide portion of the conjugate consists of at least 8 nucleotides, with a size of 15–23 nucleotides most preferred, and is capable of hybridizing to at least a portion of the nucleic acid sequence.

The oligonucleotide conjugates of the present invention can enhance the binding of the oligonucleotide to the target nucleic acid sequence relative to the binding exhibited by the oligonucleotide alone, and may lower the amount of oligonucleotide required for use as a diagnostic agent. The target nucleic acid sequence may be single stranded, double stranded, or multiply stranded.

The invention is also directed to a method for detecting a nucleic acid sequence comprising contacting the nucleic acid sequence with a composition comprising an oligonucleotide conjugate of the invention linked to a detectable label. In such an embodiment, the oligonucleotide portion consists of at least 8 nucleotides, and preferably is 15–23 nucleotides, and is capable of hybridizing to at least a portion of the nucleic acid sequence. The nucleic acid sequence may be detected in vitro or in a procaryotic or eucaryotic cell.

3.1. DEFINITIONS

A "nucleic acid sequence" as defined herein is a DNA or RNA sequence comprising one or more nucleotides, to which the oligonucleotide conjugated to the rigid structure binds.

An "oligonucleotide" as defined herein is a DNA or RNA sequence comprising at least 1 nucleotide. The oligonucleotide may be modified at the base moiety, sugar moiety, or phosphate backbone, and such modified oligonucleotides are hereinafter referred to as "oligonucleotide analogs." The oligonucleotide may also include other appending groups that may enhance cell permeability, nuclease stability, or other functions. Portions of the phosphate backbone may be replaced by other moieties.

4. BRIEF DESCRIPTION OF THE FIGURES

FIGS. 2A-1 and 2A-2 show the structure of the steroid amine hydrogen-phosphonate intermediates (compounds 1a–6a) used to synthesize the oligonucleotide-steroid amine compounds 1–6.

FIGS. 3A-1 and 3A-2 show the synthetic scheme used to prepare compound 1a.

FIGS. 4A-1 and 4A-2 show the synthetic scheme used to prepare compound 2a.

FIGS. 5A-1, 5A-2 and 5A-3 show the synthetic scheme used to prepare compound 3a.

FIGS. 6A-1 and 6A-2 show the synthetic scheme used to prepare compound 4a.

FIGS. 7A-1, 7A-2 and 7A-3 show the synthetic scheme used to prepare compound 5a.

Figures 1, 1A:
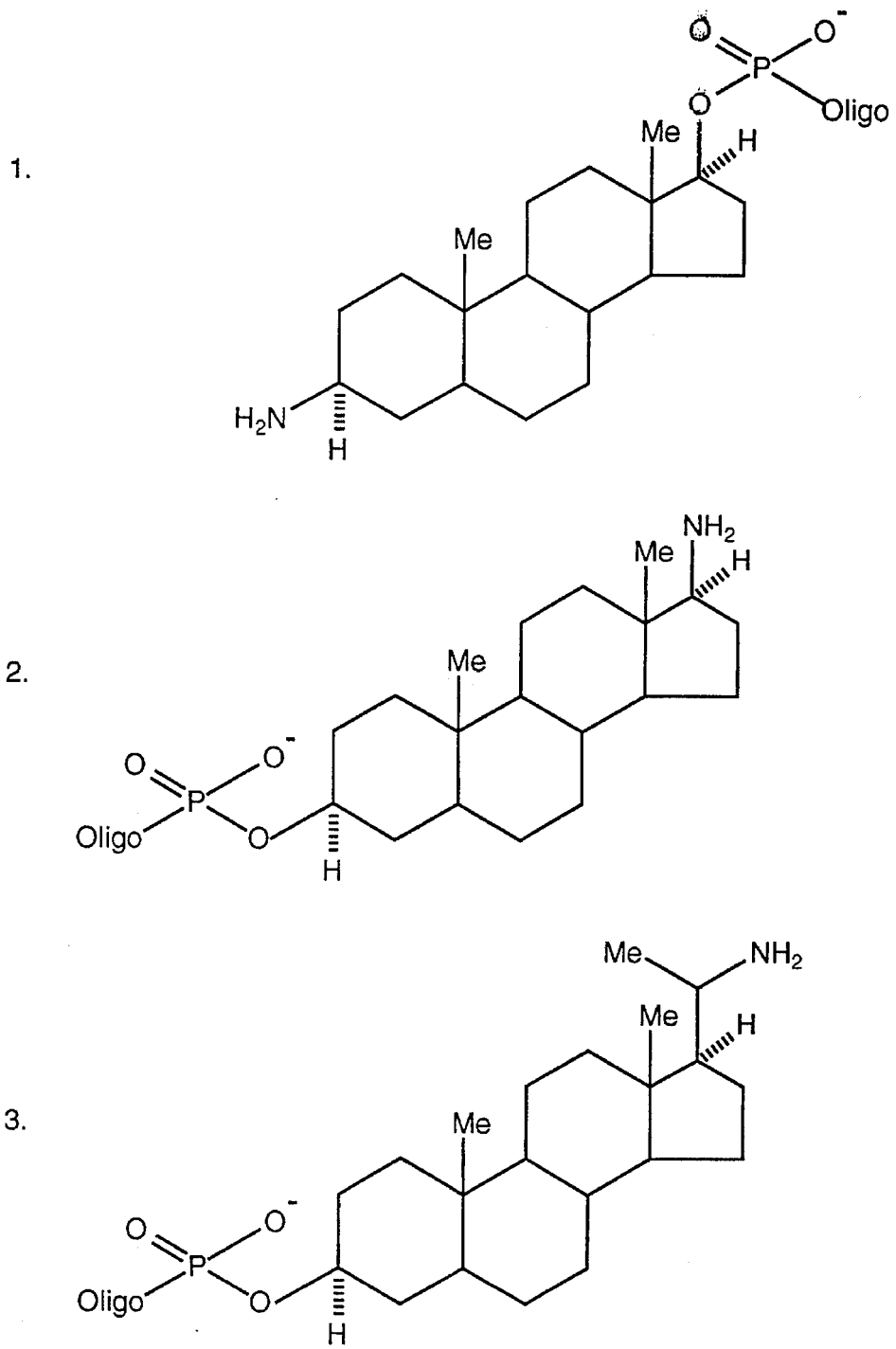
FIGS. 1A-1 and 1A-2 show the structure of the oligonucleotide-steroid amine compounds 1–6 synthesized using the procedures described in Section 6.
Figure 1A:
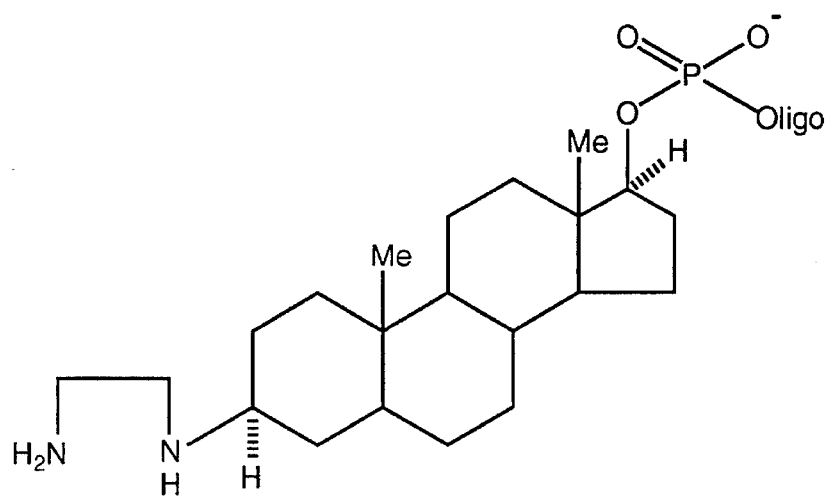
Figure 1:
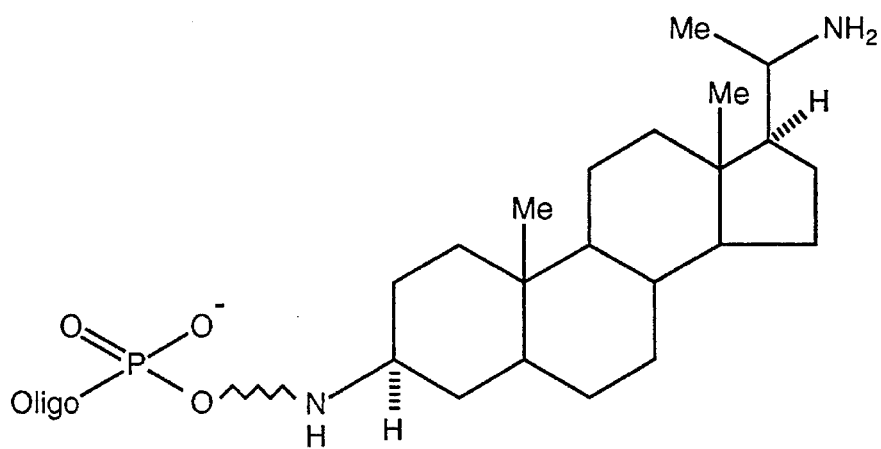
Figure 2:
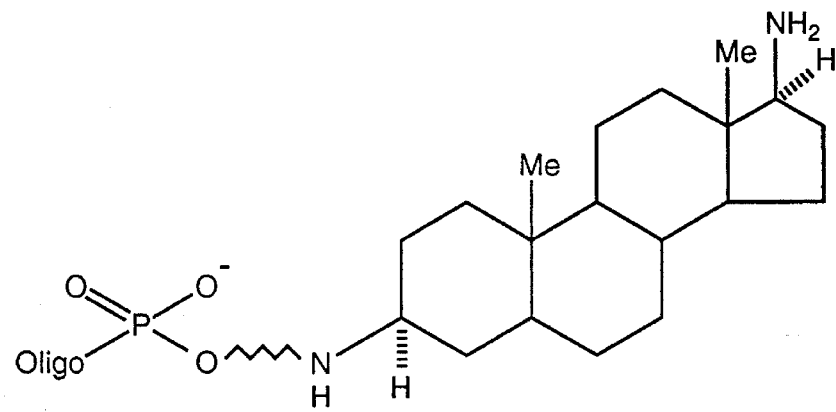
Figures 1, 2A:
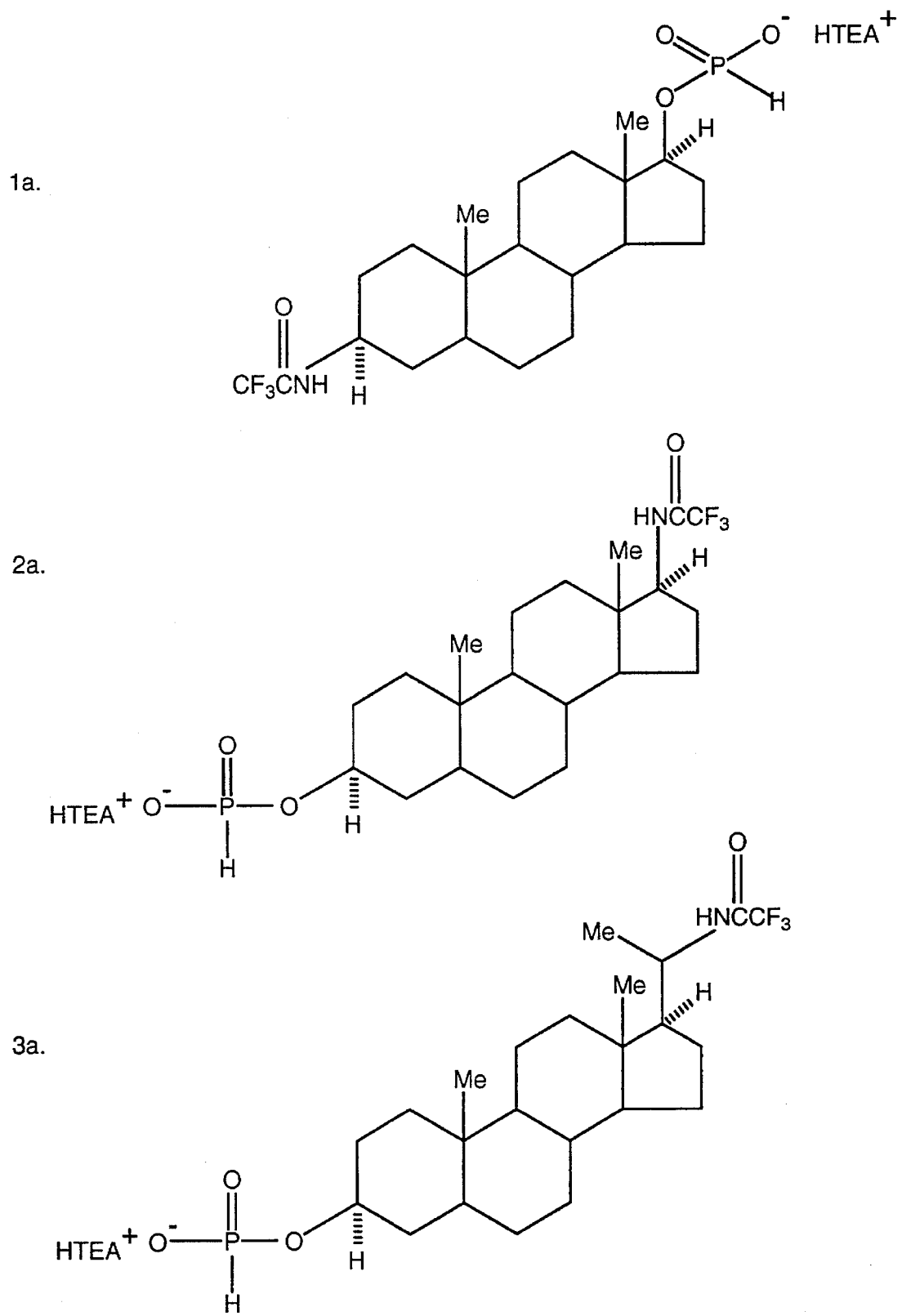
Figures 2, 2A:
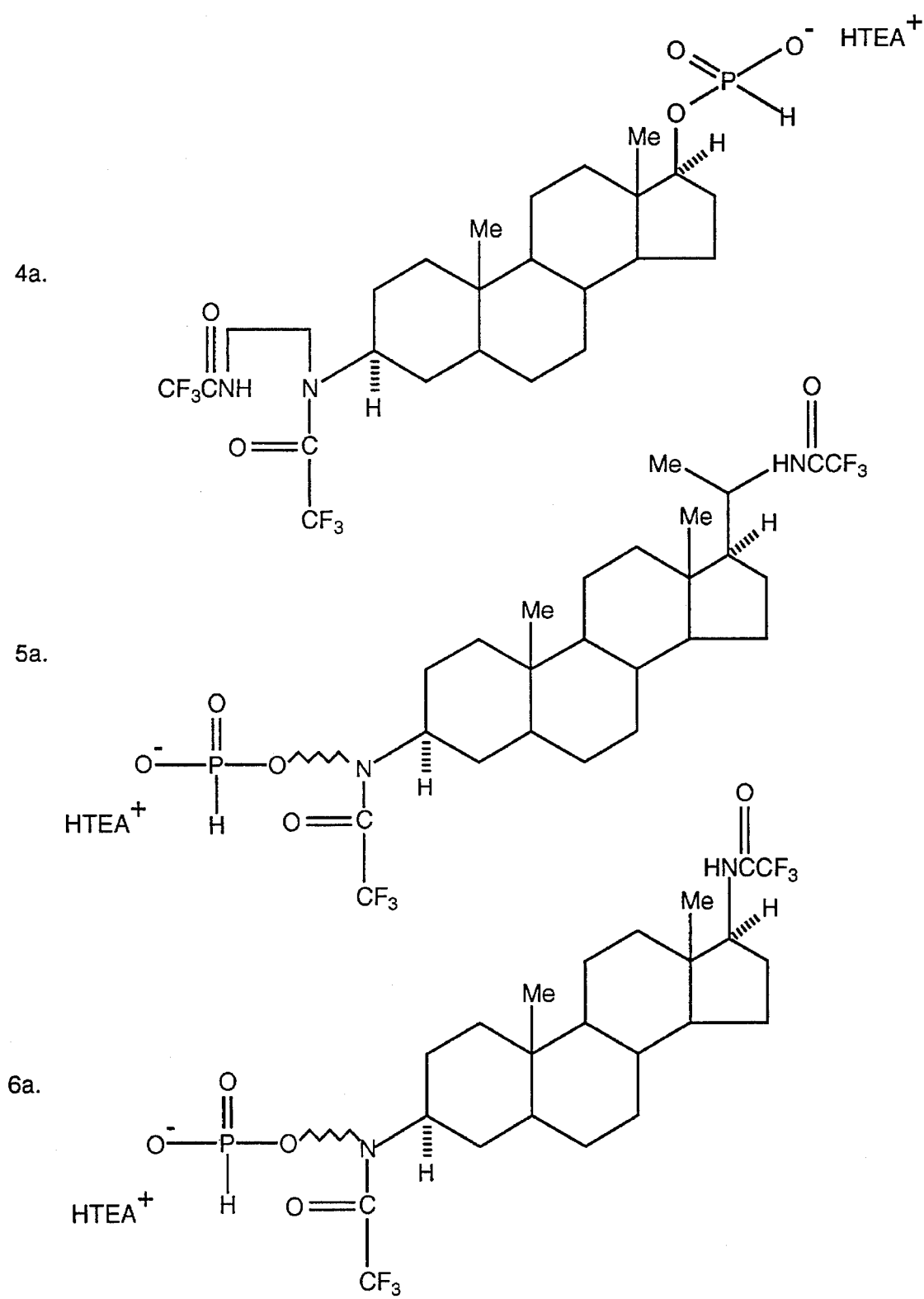
Figure 3A:
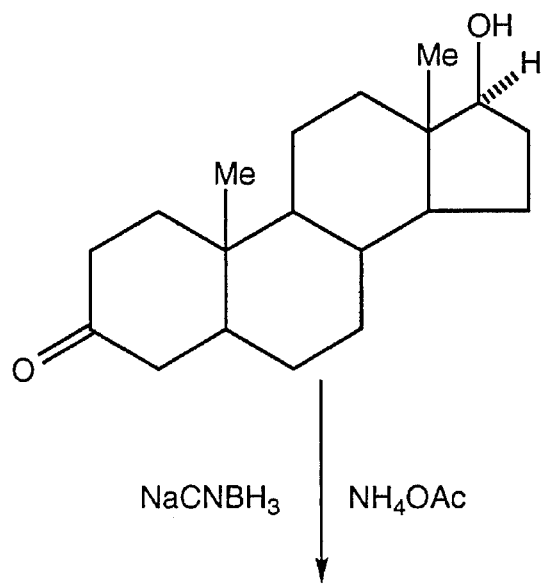
Figure 1:
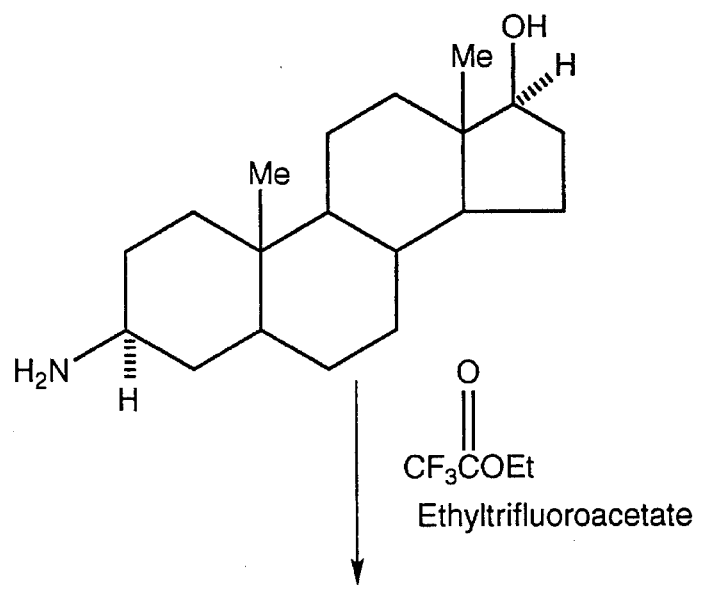
Figure 3A:
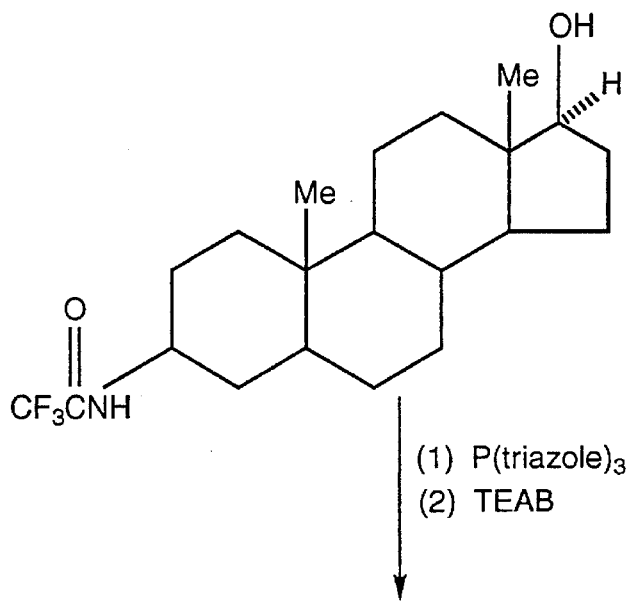
Figure 2:
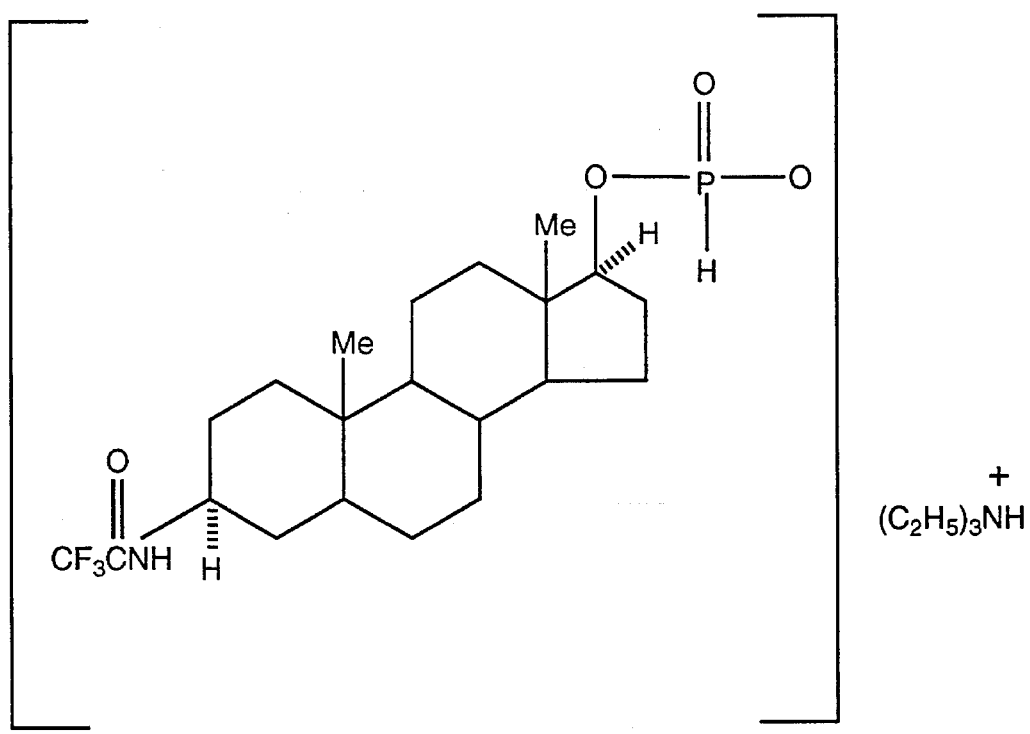
Figure 1:
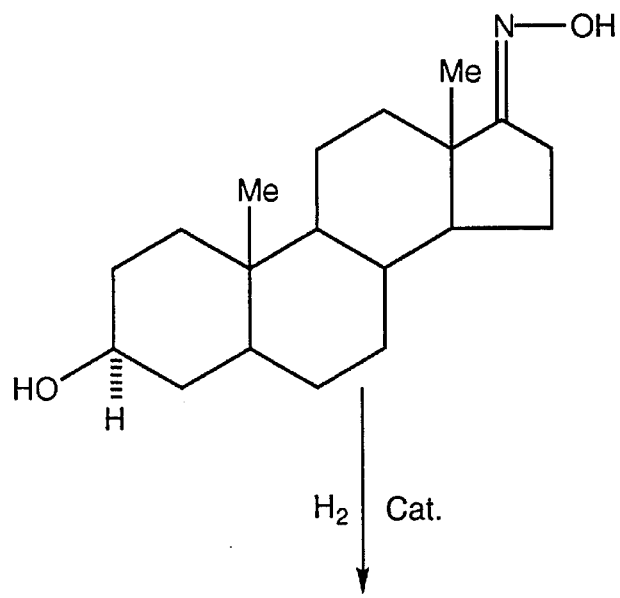
Figure 2:
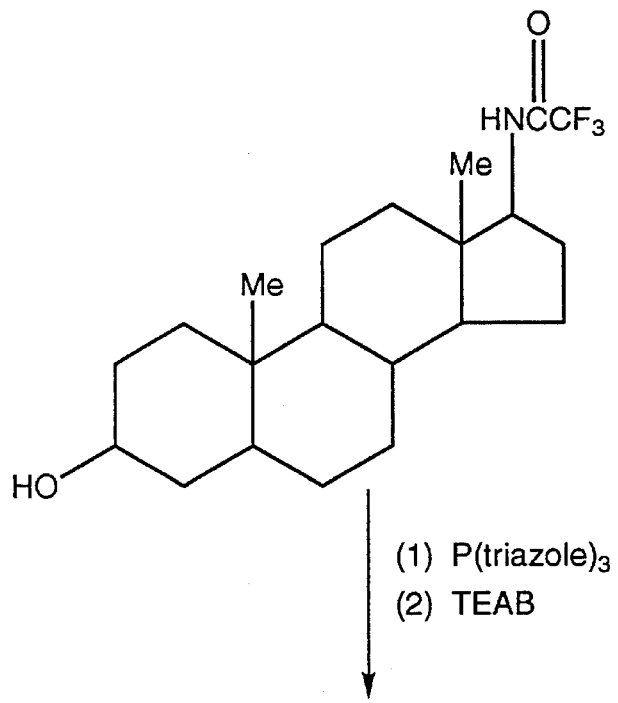

FIGS. 8A-1, 8A-2, 8A-3, and 8A-4 show the synthetic scheme used to prepare compound 6a.

5. DETAILED DESCRIPTION OF THE INVENTION

The invention is directed to an oligonucleotide or analog thereof conjugated to a molecule comprising a structure, which structure (a) is of substantially fixed conformation; (b) contains, is directly attached to, or is attached to a carbon atom that is directly attached to, a first amine; and (c) contains, is directly attached to, or is attached to an atom that is directly attached to, a phosphate, a second amine, or a cationic sulfur. Such a structure shall be referred to herein as a "rigid structure". The term "substantially fixed conformation" is used herein to mean a substantially rigid shape, the dimensions of which are not subject to substantial change. In a preferred embodiment, the rigid structure consists of at least a nonaromatic cyclic compound or substituted derivative thereof. In specific embodiments, the rigid structure can be a nonaromatic cyclic compound, asteroid, an aromatic compound, or substituted derivatives thereof.

The invention further relates to a composition that may be used as a reaction intermediate in the synthesis of an oligonucleotide conjugate of the invention, in which the rigid structure is or is contained within a steroid or substituted derivative thereof. Such a composition comprises asteroid or substituted derivative thereof which (a) contains, is directly attached to, or is attached to a carbon atom that is directly attached to, an amine; and (b) is conjugated to at least one hydrogen-phosphonate and a cation. In a specific embodiment, the steroid is conjugated to the hydrogen-phosphonate through a linking chain.

The oligonucleotide conjugates of the present invention can enhance the binding of the oligonucleotide to the target nucleic acid sequence relative to the binding exhibited by the oligonucleotide alone, and may lower the amount of oligonucleotide required for use as a diagnostic agent. The target nucleic acid sequence may be single stranded, double stranded, or multiply stranded.

The invention is also directed to a method for detecting a nucleic acid sequence comprising contacting the nucleic acid sequence with a composition comprising an oligonucleotide conjugate of the invention linked to a detectable label. In such embodiment, the oligonucleotide portion consists of at least 8 nucleotides, and preferably is 15–23 nucleotides, and is capable of hybridizing to at least a portion of the nucleic acid sequence. The nucleic acid sequence may be detected in vitro or in a procaryotic or eucaryotic cell.

5.1. THE OLIGONUCLEOTIDE CONJUGATES OF THE INVENTION

The invention is directed to an oligonucleotide or analog thereof conjugated to a molecule comprising a structure, which structure (a) is of substantially fixed conformation (b) contains, is directly attached to, or is attached to a carbon atom that is directly attached to, a first amine; and (c) contains, is directly attached to, or is attached to an atom that is directly attached to, a phosphate, a second amine, or a cationic sulfur. Such a structure shall be referred to herein as a "rigid structure". The first and second amines can be the same or different. In a preferred embodiment, the rigid structure consists of at least a nonaromatic cyclic compound or substituted derivative thereof. In specific embodiments, the rigid structure can be a nonaromatic cyclic compound, a steroid, an aromatic compound, or substituted derivatives thereof. In one embodiment, the first amine is directly attached to the rigid structure. In another embodiment, the first amine may be attached to a carbon atom which is directly attached to the structure. In yet another embodiment, the first amine is contained as part of the rigid structure. As an example of this latter embodiment, where the rigid structure consists of at least a nonaromatic cyclic compound, the amine can form part of the nonaromatic ring structure. The phosphate, cationic sulfur, or second amine of the rigid structure can be contained within the rigid structure, directly attached to the rigid structure, or linked to the rigid structure through an atom such as a carbon, oxygen, nitrogen, or sulfur.

The oligonucleotide of the conjugates of the present invention may be an oligodeoxyribonucleotide or an oligoribonucleotide. The analog of the oligonucleotide may comprise at least one modified base moiety which is selected from the group including but not limited to 5-fluorouracil, 5-bromouracil, 5-chlorouracil, 5-iodouracil, xanthine, 4-acetylcytosine, 5-(carboxyhydroxylmethyl) uracil, 5-carboxymethylaminomethyl-2-thiouridine, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), pseudouracil, 5-methyl- 2-thiouracil, 3-(3-amino-3-N-2-carboxypropyl)uracil, (acp3)w, and 2,6-diaminopurine. In another embodiment, the analog of the oligonucleotide comprises a modified sugar moiety selected from the group including but not limited to arabinose, 2-fluoroarabinose, xylulose,and hexose. In yet another embodiment, the analog of the oligonucleotide comprises a modified phosphate backbone selected from the group consisting of but not limited to a phosphorothioate, a phosphorodithioate, a phosphoramidothioate, a phosphoramidate, a phosphordiamidate, a methylphosphonate, an alkyl phosphotriester, and a formacetal or analog thereof. In yet another embodiment, the oligonucleotide is an α-anomeric oligonucleotide. An α-anomeric oligonucleotide forms specific double-stranded hybrids with complementary RNA in which contrary to the usual β-units, the strands run parallel to each other (Gautier et al, 1987, Nucl. Acids Res. 15: 6625–6641).

In a preferred embodiment, the rigid structure consists of at least a nonaromatic cyclic portion. In particular, the rigid structure may be at least a portion of a nonaromatic cyclic compound or substituted derivative thereof, examples of which include but are not limited to a monocyclic, a polycyclic, and a fused polycyclic compound. The skeleton of fixed conformation would be the ring structure. The nonaromatic cyclic compound may contain an aromatic substituent(s), but the skeleton does not involve an aromatic ring. In one embodiment, the nonaromatic cyclic compounds are n-membered rings where n=3–14. The fused polycyclic may contain from about 1 to 15 individually fused rings. The nonaromatic cyclic compound in one embodiment may contain a heteroatom in its ring skeleton. In another embodiment, the ring structure only contains carbon atoms. Specific examples of such nonaromatic cyclic compounds include but are not limited to cyclopropane, cyclobutane, cyclopentane, cyclohexane, bicycloheptane, and decalins.

The rigid structure in another embodiment may be at least a portion of an aromatic compound or substituted derivative thereof, examples of which include but are not limited to a monoaromatic or a fused polyaromatic. The rigid structure in an aromatic compound is the aromatic ring structure. In one embodiment, the aromatic compounds are n-membered rings where n=3–14. The fused polycyclic may contain from about 1 to 15 individually fused rings. The aromatic compound in one embodiment may contain a heteroatom of heteroatoms in its ring skeleton. In another embodiment, the ring structure only contains carbon atoms. Specific examples of aromatic compounds include but are not limited to benzene, naphthalene, and anthracene.

In yet another embodiment, the rigid structure may be at least a portion of a steroid or substituted derivative thereof. The structure can be the steroid ring structure. Specific examples of steroids include but are not limited to androstane, pregnane, pregnene, androstene, cholesterol, dexamethasone, estradiol, progesterone, pregnelone, corticosteroid, and testosterone.

"Substituted derivative" as used herein means that the recited groups may be substituted at any position on their structure with substituents generally used in the art. Examples of such substituents include but are not limited to alkyl, cycloalkyl, aryl, alkaryl, hydroxyalkyl, ester, ether, amide, halo, nitro, cyano, carboxylic acid, alkenyl, and heteroatom groups. Alkyl, cycloalkyl, and alkaryl groups may be substituted with groups including but not limited to ester, hydroxy, ether, halo, nitro, cyano, carboxylic acid, alkenyl, and heteroatom groups.

The amine attached to the rigid structure may be a quaternary amine(s) or cyclic amine(s) (e.g. pyrrolidine) or both. Substituents on the quaternary or cyclic amine may be homogeneous or heterogeneous and may be selected from the group including but not limited to a hydrogen, alkyl, cycloalkyl, aryl, alkaryl, hydroxy, and substituted derivatives thereof. Alternatively, the amine may have the formula $R_1NR_2$ in which $R_1$ and $R_2$ are selected from the group including but not limited to hydrogen, alkyl, cycloalkyl, aryl, alkaryl, hydroxy, and substituted derivatives thereof.

The rigid structure may be conjugated to the oligonucleotide at the base moiety, the sugar moiety, and/or the phosphate moiety using methods known in the art. For example, the rigid structure may be conjugated to the oligonucleotide using the hydrogen-phosphonate procedure (Froehler et al., 1986, Nucl. Acids Res. 14: 5399–5407). In another embodiment, the oligonucleotide may be linked to the rigid structure at any base, sugar (2', 3', and/or 5' position) or phosphate group of the oligonucleotide using amidite chemistry (Froehler, 1986, Tetrahedron Lett. 27: 5575–5578 and Caruthers et al., 1982, Genetic Engineering, J. K. Setlow and A. Hollaender eds, Plenum Press, New York, vol. 4, pp. 1–17). Alternatively, the rigid structure amine may be linked to the oligonucleotide at any base, sugar (2', 3', and/or 5' position) or phosphate moiety of the oligonucleotide via a linkage such as an amide linkage (see Tessler et al., 1989, J. Amer. Chem. Soc. 111: 7226–7232; Tessler et al., 1989, J. Amer. Chem. Soc. 111: 7221–7226; and Tessler et al., 1989, J. Amer. Chem. Soc. 111: 6966–6976 for specific examples). Specifically, an oligonucleotide containing an amine is allowed to react with the amine on the rigid structure containing a carboxylic acid, ester or the like.

In a specific embodiment, the oligonucleotide may be conjugated to the rigid structure via a linking chain. In one embodiment, the linking chain/comprises an aliphatic, alkyl, or branched aliphatic alkyl, or aromatic or substituted derivative thereof, or a heteroatom containing an alkyl or branched chain or aromatic or substituted derivative thereof of about 1 to about 20 carbon atoms. The linking chain may include functionalities such as oxy, non-oxocarbonyl, an aldehyde or ketone, and nitrogen or sulfur moieties such as imino, thiono, thio, amino, diazo, hydrazino, oximo moieties.

5.1.1. OLIGONUCLEOTIDE-STEROID AMINE CONJUGATES

In a particular aspect of the invention, the rigid structure of the oligonucleotide conjugates of the invention is at least a portion of asteroid or substituted derivative thereof. In a specific embodiment, the oligonucleotide may be conjugated to such steroid amine via a linking chain. In one embodiment, the linking chain comprises an aliphatic, alkyl, or branched aliphatic alkyl, or aromatic or substituted derivative thereof, or a heteroatom containing an alkyl or branched chain, or an aromatic or substituted derivative thereof of about 1 to about 20 carbon atoms. The linking chain may include functionalities such as oxy, non-oxo-carbonyl, an aldehyde or ketone, and nitrogen or sulfur moieties such as imino, thiono, thio, amino, diazo, hydrazino, oximo moieties.

The steroid may be selected from the group including but not limited to androstane, pregnane, pregnene, androstene, cholesterol, dexamethasone, estradiol, progesterone, pregnelone, corticosteroid, testosterone, and substituted derivatives thereof. In a specific embodiment, the steroid is androstane. The amine(s) may be attached to any position on the androstane. In one embodiment, the amine may be attached to the 3-position and/or the 17-position of the androstane. The amines when attached to the 3-position and 17-position of the androstane may be cis or trans to one another. In a preferred embodiment, the amines are cis to one another. In another embodiment, the steroid is pregnane. The amine(s) may be attached to any position on the pregnane. In one embodiment, the amine may be attached to the 3-position and/or the 20-position of the pregnane.

The steroid amine may be conjugated to the oligonucleotide at the base moiety, the sugar moiety, and/or the phosphate using methods known in the art. Examples of such procedures are disclosed in Section 5.1., supra.

In one embodiment, the steroid amine may be conjugated to the oligonucleotide at the 2', 3', and/or 5' position of any sugar moiety of the oligonucleotide by allowing the oligonucleotide to react with a composition comprising asteroid amine conjugated to a hydrogenphosphonate, and a cation using the procedure described by Froehler et al. (1986, Nucl. Acids Res. 14: 5399–5407).

The amine may be a quaternary amine or cyclic amine (e.g. pyrrolidine) or both. Substituents on the quaternary or cyclic amine may be homogeneous or heterogeneous and may be selected from the group including but not limited to a hydrogen, alkyl, cycloalkyl, aryl, alkaryl, hydroxy and substituted derivatives thereof. Alternatively, the amine may have the formula $R_1NR_2$ in which $R_1$ and $R_2$ are selected from the group including but not limited to hydrogen, alkyl, cycloalkyl, aryl, alkaryl, hydroxy and substituted derivatives thereof, and a removable protecting group. Suitable protecting groups include but are not limited to trifluoroacetyl, acyl, isobutyryl, and benzoyl (see Greene, in Protective Groups in Organic Synthesis, John Wiley & Sons, New York, 1981 for some further examples). The cation may be an intermolecular cation which may be selected from the group including but not limited to 1,5-diazabicyclobicyclo[4.3.0]non-5-ene quaternary ammonium, 1,4-diazabicyclo[2.2.2]octane quaternary ammonium, 1,8-diazabicyclo[5.4.0]undec-7-ene quaternary ammonium, tetrabutylammonium, tributylammonium, triethylammonium, diisopropylethylammonium, 1,8-bis-dimethylaminonaphthalene quaternary ammonium, benzyltrimethylammonium, and benzyltriethylammonium ion. Alternatively, the cation may arise from an intramolecular cation such as a quarternized amine for example.

In a specific embodiment, the hydrogen-phosphonate may be conjugated to the steroid amine via a linking chain. In one embodiment, the linking chain comprises an aliphatic, alkyl, or branched aliphatic alkyl, or an aromatic or substituted derivative thereof, or a heteroatom containing an alkyl or branched chain or aromatic or substituted derivative of about 1 to about 20 carbon atoms. The linking chain may include functionalities such as oxy, non-oxo-carbonyl, an aldehyde or ketone, and nitrogen or sulfur moieties such as imino, thiono, thio, amino, diazo, hydrazino, oximo moieties.

Specific examples of compositions comprising a steroid containing or attached directly or through a carbon atom to an amine, conjugated to a hydrogen-phosphonate, and a cation are disclosed in Section 6, infra and include 3-β-N-trifluoroacylamino- 5α-androstan-17β-O-yl-hydrogen-phosphonate triethylammonium salt, 17β-N-trifluoroacylamino-5α-androstan- 3β-O-yl-hydrogen-phosphonate triethylammonium salt, 5-N-trifluoroacylamino- 5α-pregnan-3β-O-yl-hydrogen-phosphonate triethylammonium salt, 3β-[N-(2-N-trifluoroacylaminoethyl )-N-trifluoroacylamino]-5α-androstan- 3β-O-yl-hydrogen-phosphonate triethylammonium salt, 5-N-trifluoroacyl- 5-(20-N-trifluoroacylamino-5α-pregnan-3β-N-yl )-aminopentan-1-O-yl-hydrogen-phosphonate triethylammonium salt, and 5-N-trifluoroacyl-5-(17β-N-trifluoroacylamino-5α-androstan-3β-N-yl)-aminopentan-1-O-yl-hydrogen-phosphonate triethylammonium salt.

5.2. USES OF THE OLIGONUCLEOTIDE CONJUGATES OF THE INVENTION

The rigid structure can bind a second nucleic acid sequence through ionic bonding and/or other Van der Waals interactions. In particular, the rigid structure may bind through ionic bonding via the positively charged amine group(s) on the structure (either by quaternization of the amine groups or protonation at physiological pH) and the negatively charged phosphate groups on the nucleic acid sequence. If the rigid structure comprises two or more amines, the amines can interact with two or more separate phosphate chains. In a specific embodiment, the rigid structure binds through nonintercalative interactions. The rigid structure may bind to the nucleic acid sequence through nonintercalative interactions which may include inducing a kink in the nucleic acid sequence.

In a particular aspect, the oligonucleotide portion of the conjugates of the invention comprises a sequence complementary and capable of hybridizing to at least a portion of a DNA or RNA sequence of the pathogenic organism.

An effective amount of an oligonucleotide conjugate of the invention in which the oligonucleotide or analog thereof consists of at least 8 nucleotides, is capable of hybridizing to at least a portion of a nucleic acid sequence, and is detectably labeled, may be used as a diagnostic agent by hybridizing to its specific complementary nucleic acid sequence. In one embodiment, the composition may be used to detect a nucleic acid sequence in vitro. In another embodiment, the composition may be used to detect a nucleic acid sequence in a procaryotic or eucaryotic cell. The detectable label may be linked directly or indirectly (e.g. by attachment to the rigid structure) to the oligonucleotide. The detectable label may be selected from the group including but not limited to a radioactive group, an enzyme, a fluorescent group, and an antibody. The labelled composition is hybridized to the complementary nucleic acid sequence and is detected using procedures known in the art. In a specific aspect, the rigid structure binds to a second nucleic acid sequence, which binding can be in a nonintercalative manner. The first and second nucleic acid sequences may be the same, may overlap, or may be distinct.

The following examples are presented by way of illustration, not by way of limitation.

6. PREPARATION OF OLIGONUCLEOTIDE AMINE CONJUGATES

The preparation of six oligonucleotide steroid amine compounds, each containing the 14 mer DNA strand 5'-TCTCCCTCTCTTTT- 3' is disclosed. The structures of these six conjugates (1–6) are shown in FIG. 1. These conjugates were prepared by allowing the salts of the steroid amine or diamine hydrogen-phosphonate intermediates (1a–6a), shown in FIG. 2 to react with the oligonucleotide. The reaction schemes used to prepare such intermediates are shown in FIGS. 3–8. In the examples disclosed herein, methods used to prepare the steroid amine or steroid diamine hydrogenphosphonates and methods used to incorporate these steroid amine or steroid diamine hydrogen- phosphonates into the oligonucleotide are described below.

6.1. PREPARATION OF 3-β-N-TRIFLUOROACYLAMINO-5α-ANDROSTAN-17β-O-YL-HYDROGEN-PHOSPHONATE TRIETHYLAMMONIUM SALT (1a)

Figure 4A:
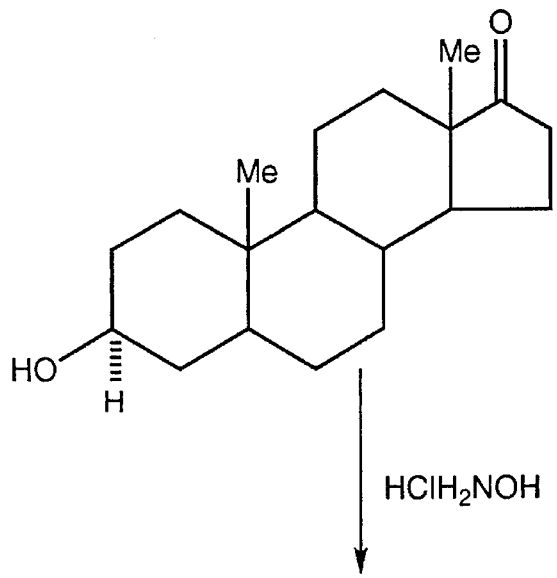
Figure 4A:
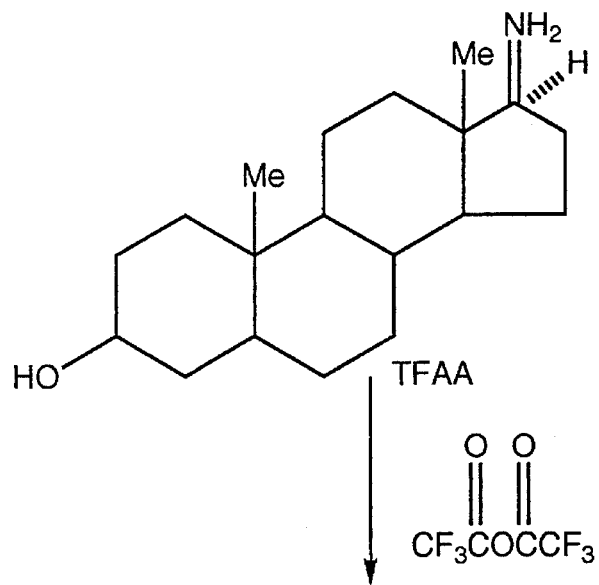
Figures 3, 4A:
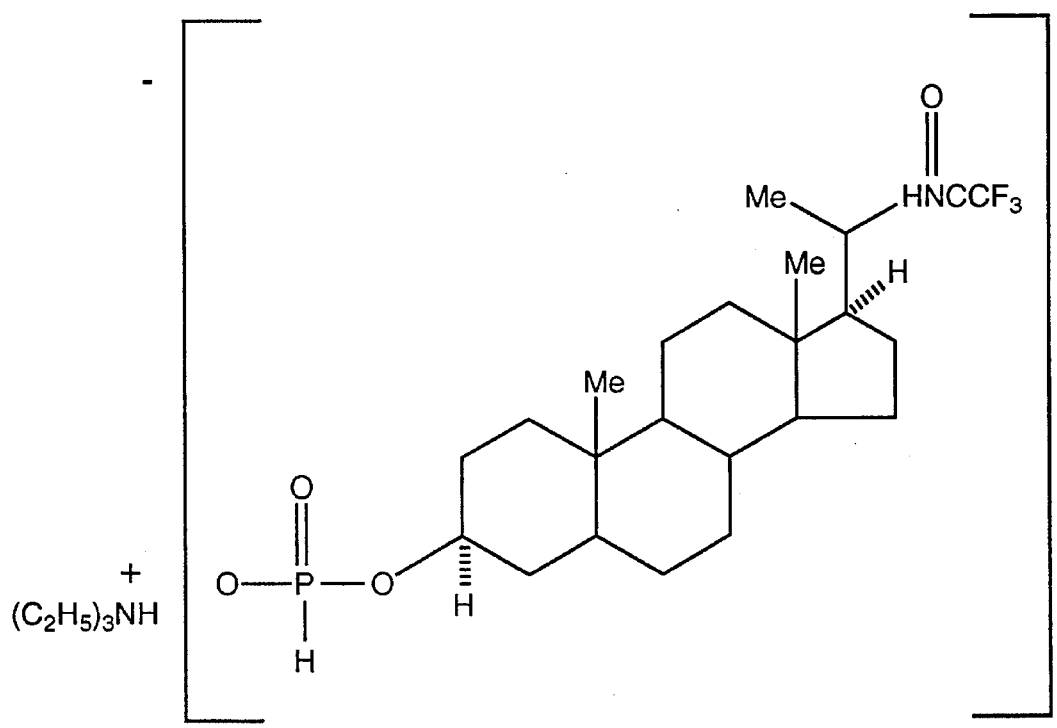

The reaction scheme used to prepare compound 1a is shown in FIG. 3. Briefly, the reaction scheme first involved the preparation of 3β-amino-17β-hydroxy-5α-androstane by the reductive amination of the 3-keto group on 17β-hydroxy-5α-androstan-3-one. The amine on 3β-amino-17β-hydroxy-5α-androstane was protected by trifluoroacetylation resulting in the formation of 17β-hydroxy-3β-N-trifluoroacylamino- 5α-androstane. The third step involved the formation of compound 1a.

6.1.1. 3β-AMINO-17β-HYDROXY-5α-ANDROSTANE

3β-Amino-17β-hydroxy-5α-androstane was prepared by the procedure of Boutigue et al. (1973, Bull. Soc. Chim. France 750–753). 17β-Hydroxy-5α-androstan-3-one (403 mg, 1.39 mmol) (Aldrich Chemical Company) was added to 862 mg of ammonium acetate (11.2 mmol, 8.06 equiv.) in 16.0 mL dry methanol (MeOH), followed by 104 mg (1.65 mmol, 1.19 equiv.) of sodium cyanoborohydride. After stirring at room temperature for 15 h, the reaction was concentrated under reduced pressure. The residue was partitioned between methylene chloride and aqueous 1N sodium hydroxide (NaOH), shaken, and separated. The organic layer was washed with water, dried over sodium sulfate, filtered, and concentrated under reduced pressure. The product was used without further purification.

6.1.2.
17β-HYDROXY-3β-N-TRIFLUOROACYLAMINO-5α-ANDROSTANE

The trifluoroacylation of amines using ethyl trifluoroacetate was carried out using the procedure of Curphey (1979, J. Org. Chem. 44: 2805–2807). Triethylamine (TEA) (3.0 mL, 21.5 mmol, 15.5 equiv.) was added to crude 3β-amino-17β-hydroxy-5α-androstane (1.39 mmol) in 8.0 mL dry methanol, followed by 3.21 mL (27.0 mmol, 19.4 equiv.) of ethyl trifluoroacetate (Aldrich). After stirring for 22 h at room temperature, the reaction was concentrated on a rotary evaporator. The residue was partitioned between methylene chloride and aqueous 1N hydrogen chloride (HCl), shaken, and separated. The organic layer was washed with water, saturated aqueous sodium bicarbonate, water, dried over sodium sulfate, filtered, and concentrated under reduced pressure. The product was purified by flash chromatography (Still et al., 1978, J. Org. Chem. 43: 2923–2925) on a 25 mm column using first one column volume of methylene chloride, then one column volume of 5% ethyl acetate (EtOAc) in methylene chloride, and then 10% EtOAc in methylene chloride as eluants. Isolation of the product afforded 339 mg (62.9% yield over two steps) of product.

6.1.3.
3β-N-TRIFLUOROACYLAMINO-5α-ANDROSTAN-17β-O-YL-HYDROGEN-PHOSPHONATE TRIETHYLAMMONIUM SALT (1a)

A solution of 2M trichlorophosphine ($PCl_3$) (0.588 mL) in methylene chloride (1.18 mmol) was added to a rapidly stirred mixture of 1,2,4-triazole (328 mg, 4.75 mmol) and 1.18 mL of anhydrous 4-methylmorpholine (10.7 mmol) in 6.0 mL of dry methylene chloride. The mixture was then cooled in an icewater bath for 30 min. A solution of 114 mg of 17β-hydroxy- 3β-N-trifluoroacylamino-5α-androstane (0.294 mmol, previously concentrated from dry pyridine) in 1.8 mL of dry pyridine was added dropwise to the above mixture over several minutes. The reaction was stirred for 20 min., and then poured onto 42 mL of cold 1M aqueous triethylammonium bicarbonate (TEAB, pH=9.0). The mixture was rapidly stirred for 15 min., and then extracted with 2×42 mL of methylene chloride. The combined organics were washed with 50 mL 1M aqueous TEAB, dried over sodium sulfate, filtered, and concentrated under reduced pressure. The residue was purified by flash chromatography on a 20 mm column using one column volume of 1% TEA in methylene chloride, then one column volume of 1% TEA and 5% MeOH in methylene chloride, and then 1% TEA and 10% MeOH in methylene chloride. The procedure afforded 106 mg (65.4% yield) of product as a colorless foam.

6.2. PREPARATION OF 17β-N-TRIFLUOROACYLAMINO-5α-ANDROSTAN-3β-O-YL-HYDROGEN-PHOSPHONATE TRIETHYLAMMONIUM SALT (2a)

Figure 4:
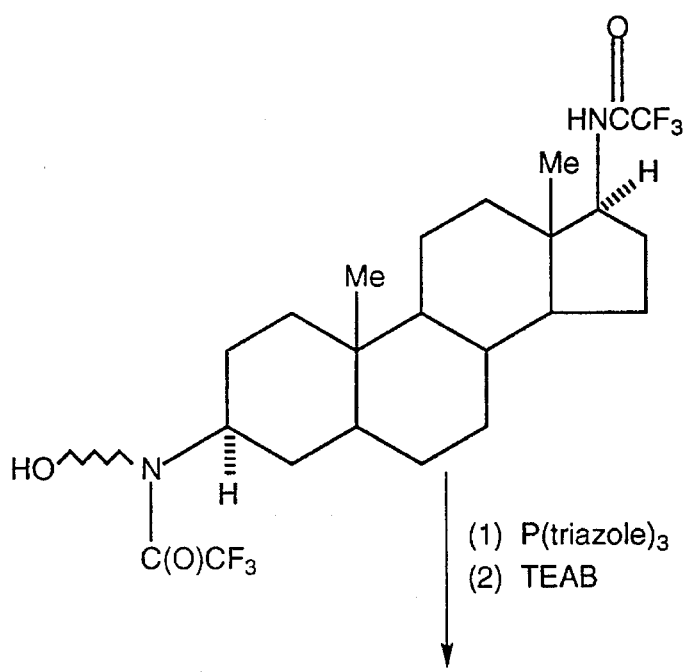

The reaction scheme used to prepare compound 1a is shown in FIG. 4. Briefly, the reaction scheme first involved the preparation of 3β-hydroxy-5α-androstan-17-oxime. 3β-Amino-17β-hydroxy-5α-androstane was prepared by the reduction of the oxime. The amine on 17β-amino-3β-hydroxy- 5α-androstane was protected by trifluoroacetylation resulting in the formation of 17β-N-trifluoroacylamino-3β-hydroxy-5α-androstane. The fourth step involved the formation of compound 2a.

6.2.1.
3β-HYDROXY-5α-ANDROSTAN-17-OXIME

3β-Hydroxy-5α-androstan-17-oxime was prepared generally using published procedure (Janot et al., 1962, Bull Soc. Chim. France, 111–118). Specifically, 534 mg (7.68 mmol) of hydroxylamine hydrochloride was added to 882 mg of 3β-hydroxy- 5α-androstan-17-one (3.04 mmol, first concentrated from dry pyridine) in 6.0 mL of dry pyridine. After stirring for 23 h, the reaction was partitioned between diethyl ether and water, shaken, and separated. The organic layer was washed with a saturated aqueous solution of NaCl, dried over sodium sulfate, filtered, and concentrated under reduced pressure. The crude solid product was taken on without further purification.

6.2.2.
17β-AMINO-3β-HYDROXY-5α-ANDROSTANE

The procedure of Chien et al. (1964, J. Org. Chem. 29: 315–318) was used for the reduction of the oxime. A suspension of 250 mg of Pt(IV) oxide (Adams catalyst, from Aldrich) in 20 mL acetic acid was hydrogenated at 40 psi $H_2$ in a Parr reaction vessel with stirring at room temperature for 45 min. A solution of crude 3β-hydroxy-5α-androstan-17-oxime (3.04 mmol) in 7.0 mL acetic acid was then added. The stirred mixture was hydrogenated at 40 psi of $H_2$ for 22 h at room temperature. The catalyst was removed by filtration through Celite. The filtrate was concentrated, and the residue was partitioned between methylene chloride and 1N sodium hydroxide, shaken, and separated. The organic layer was washed with water, dried over sodium sulfate, filtered, and concentrated under reduced pressure. No further purification was undertaken.

6.2.3.
17β-N-TRIFLUOROACYLAMINO-3β-HYDROXY-5α-ANDROSTANE

Trifluoroacetic anhydride (3.0 mL) was added to crude 17β-amino-3β-hydroxy-5α-androstane (3.04 mmol, first concentrated from dry pyridine) in 5 mL of dry pyridine. An additional 2.0 mL dry pyridine was added to aid in stirring. After 3.5 h, the reaction was partitioned between diethyl either and 1N aqueous HCl, shaken and separated. The organic layer was successively washed with 1N aqueous HCl, water, saturated aqueous sodium bicarbonate, dried over sodium sulfate, filtered, and concentrated under reduced pressure. The residue was refluxed in methanol for 56 h and concentrated. The residue was purified by flash chromatography on a 25 mm column using first one column volume of methylene chloride, then one column volume of 5% ethyl acetate in methylene chloride, and then 10% ethyl acetate in methylene chloride as eluants. Isolation and concentration of the product afforded 545 mg (46.3% yield over three steps, from 3β-hydroxy-5α-androstan-17-one) of product.

6.2.4.
17β-N-TRIFLUOROACYLAMINO-5α-ANDROSTAN-3β-O-YL HYDROGEN-PHOSPHONATE TRIETHYLAMMONIUM SALT (2a)

The procedure used to prepare compound 2a was basically the same as that used for the preparation of compound 1a except that 114 mg (0.294 mmol) of 17β-N-trifluoroacylamino- 3β-hydroxy-5α-androstane was used. After the TEAB workup, the organic layer was dried and concentrated. The residue was purified by flash chromatography on a 20 mm column using one column volume of 1% TEA in methylene chloride, then one column volume of 1% TEA and 5% MeOH in methylene chloride, and then 1% TEA and 10% MeOH in methylene chloride as eluants. The procedure afforded 112 mg (69.1% yield) of product as a colorless foam.

6.3. PREPARATION OF 20-N-TRIFLUOROACYLAMINO-5α-PREGNAN-3β-O-YL-HYDROGEN-PHOSPHONATE TRIETHYLAMMONIUM SALT (3a)

Figure 5A:
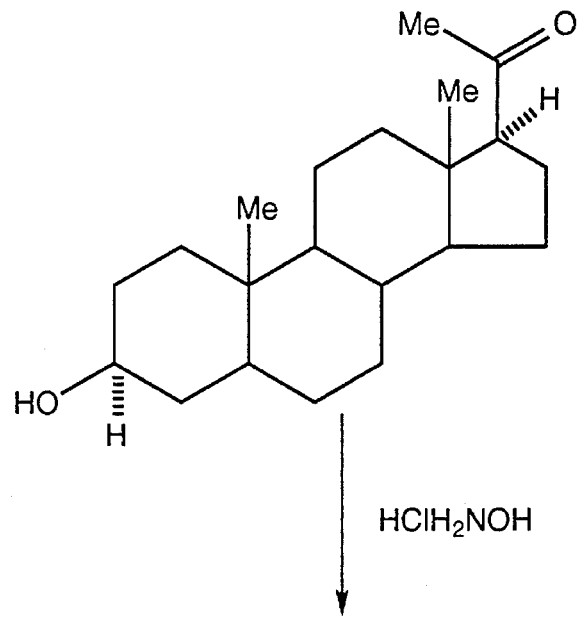
Figure 1:
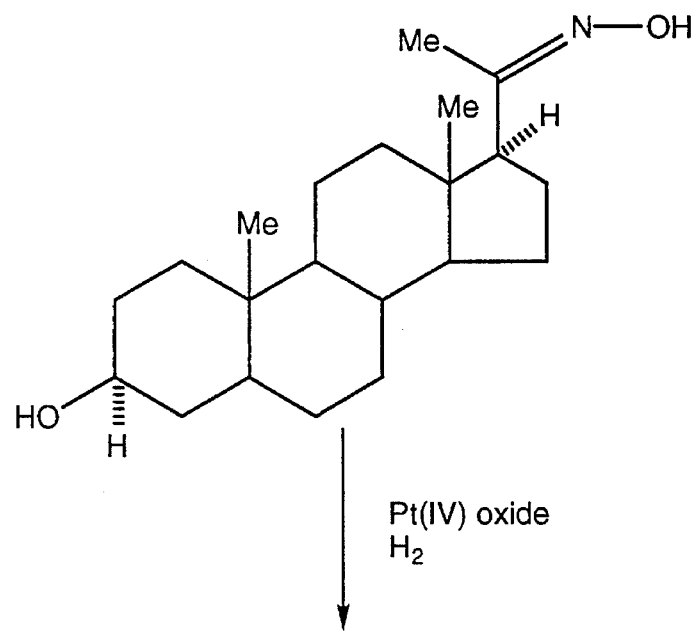
Figure 5A:
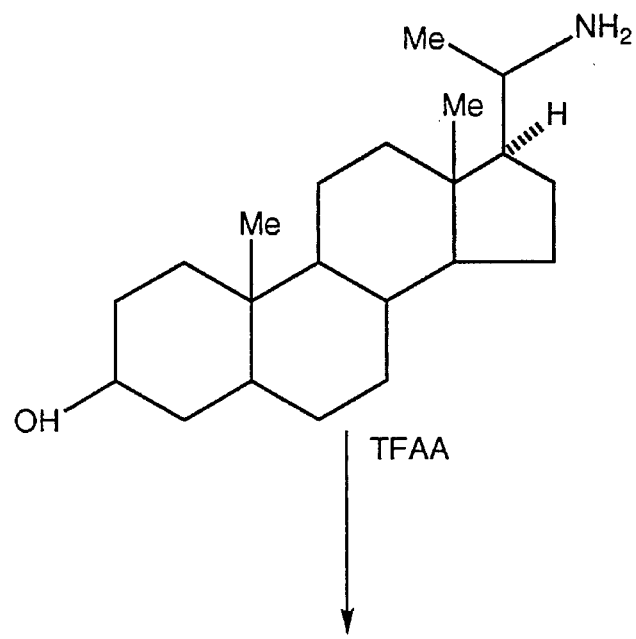
Figure 2:
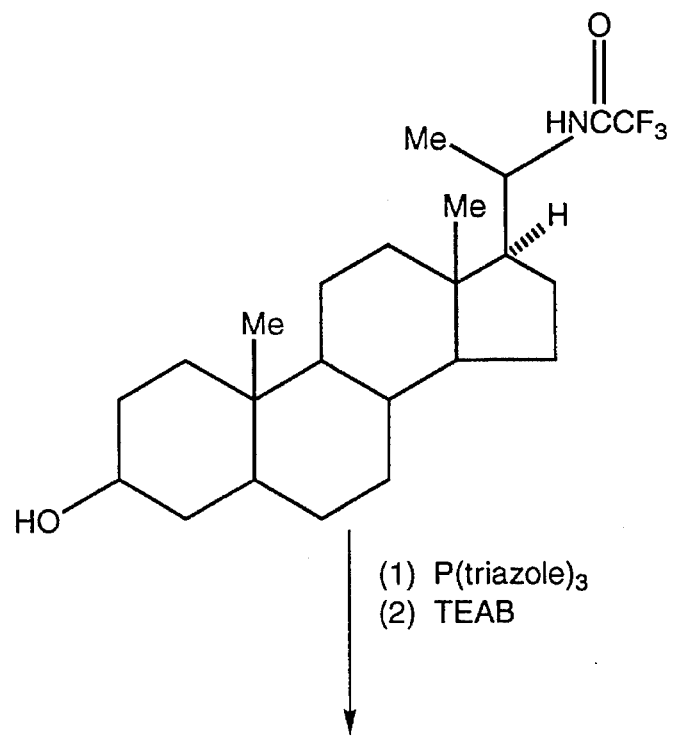
Figures 3, 5A:
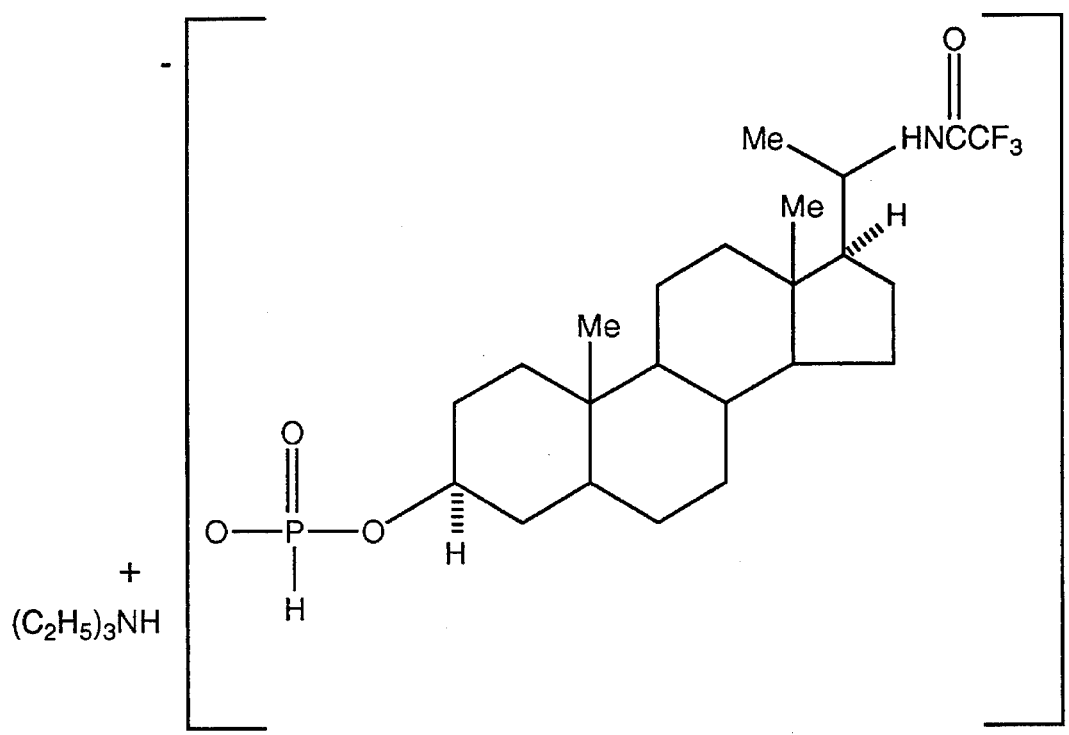

The reaction scheme used to prepare compound 3a is shown in FIG. 5. Briefly, the reaction scheme first involved the preparation of 3β-hydroxy-5α-pregnan-20-oxime. 20-Amino-3β-hydroxy-5α-pregnane was prepared by the reduction of the oxime. The amine on 20-amino-3β-hydroxy-5α-pregnane was protected by trifluoroacetylation resulting in the formation of 20-N-trifluoroacylamino-3β-hydroxy-5α-pregnane. The fourth step involved the formation of compound 3a.

6.3.1. 3β-HYDROXY-5α-PREGNAN-20-OXIME

3β-Hydroxy-5α-pregnan-20-oxime was prepared generally using published procedures (Janot et al., 1962, Bull Soc. Chim. France, 111–118). Specifically, 528 mg (7.60 mmol) of hydroxylamine hydrochloride was added to 967 mg (3.04 mmol, first concentrated from dry pyridine) of 3β-hydroxy-5α-pregnan-20-one (Sigma Chemical Co.) in 6.0 mL of dry pyridine. After stirring the reaction mixture for 20 h, the reaction mixture was partitioned between diethyl ether and water, shaken, and separated. The organic layer was dried over sodium sulfate, filtered, and concentrated under reduced pressure. The crude solid product was taken on without further purification.

6.3.2. 20-AMINO-3β-HYDROXY-5α-PREGNANE

The procedure of Chien et al. (1964, J. Org. Chem. 29: 315–318) was used for the reduction of the oxime. A suspension of 250 mg of Pt(IV) oxide (Adams catalyst, from Aldrich) in 20 mL acetic acid was hydrogenated at 40 psi $H_2$ in a Parr reaction vessel with stirring at room temperature for 45 min. The crude 3β-hydroxy-5α-pregnan-20-oxime (3.04 mmol) was then added as a solid. The stirred reaction mixture was hydrogenated at 40 psi of $H_2$ for 19.5 h at room temperature. The catalyst was removed by filtration through Celite. The filtrate was concentrated, and the residue was partitioned between methylene chloride and 1N aqueous sodium hydroxide, shaken, and separated. The organic layer was washed with water, dried over sodium sulfate, filtered, and concentrated under reduced pressure. The crude product was taken on without further purification.

6.3.3. 20-N-TRIFLUOROACYLAMINO-3β-HYDROXY-5α-PREGNANE

20-Amino-3β-hydroxy-5α-pregnane was first concentrated from dry pyridine. Trifluoroacetic anhydride (3.0 mL) was then carefully added to 3.04 mmol of crude 20-amino-3β-hydroxy-5α-pregnane resuspended in 5.0 mL dry pyridine. After stirring the reaction mixture at room temperature for 3.5 h, the reaction mixture was partitioned between diethyl ether and 1N aqueous HCl, shaken and separated. The organic layer was successively washed with 1N aqueous HCl, water, saturated aqueous sodium bicarbonate, dried over sodium sulfate, filtered, and concentrated under reduced pressure. The residue was refluxed in 15.0 mL methanol for 26 h and then concentrated. The residue was purified by flash chromatography on a 25 mm column using first one column volume of methylene chloride, then one column volume of 5% ethyl acetate in methylene chloride, and then 10% ethyl acetate in methylene chloride as eluants. Isolation and concentration of the product afforded 668 mg (52.9% yield over three steps, from 3β-hydroxy-5α-pregnan-20-one) of product.

6.3.4. 20-N-TRIFLUOROACYLAMINO-5α-PREGNAN-3β-O-YL-HYDROGEN-PHOSPHONATE TRIETHYLAMMONIUM SALT (3a)

The procedure used to prepare compound 3a was basically the same as that used for the preparation of compounds 1a and 2a except that 122 mg (0.294 mmol) of 20-N-trifluoroacylamino- 3β-hydroxy-5α-pregnane was used. After the TEAB workup, the organic layer was dried and concentrated. The residue was purified by flash chromatography on a 20 mm column using one column volume of 1% TEA in methylene chloride, then one column volume of 1% TEA and 5% MeOH in methylene chloride, and then 1% TEA and 10% MeOH in methylene chloride. The procedure afforded 88.4 mg (51.7% yield) of product.

6.4. PREPARATION OF 3β-[N-(2-N-TRIFLUOROACYLAMINOETHYL)-N-TRIFLUOROACYLAMINO] -5α-ANDROSTAN-3β-O-YL-HYDROGEN-PHOSPHONATE TRIETHYLAMMONIUM SALT (4a)

Figure 6A:
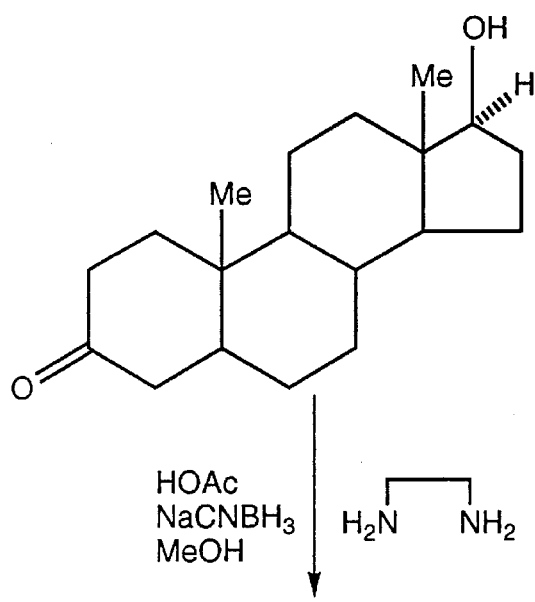
Figure 1:
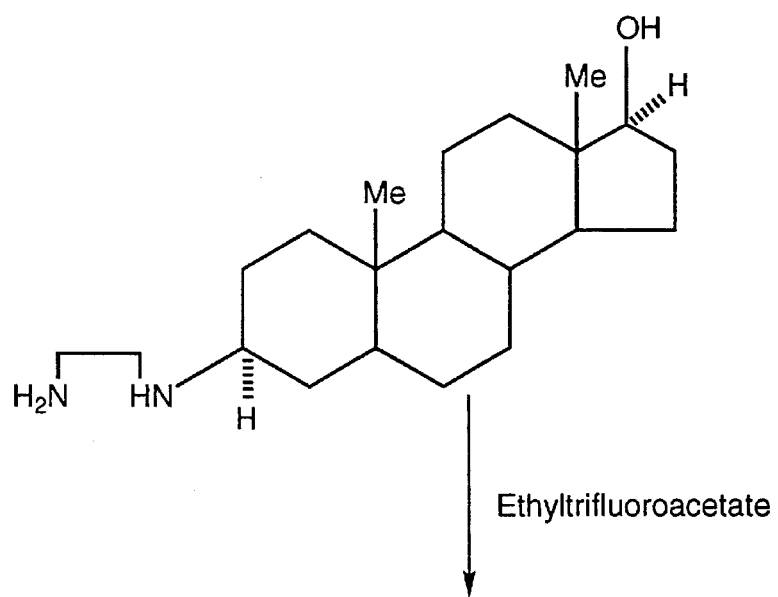
Figure 6A:
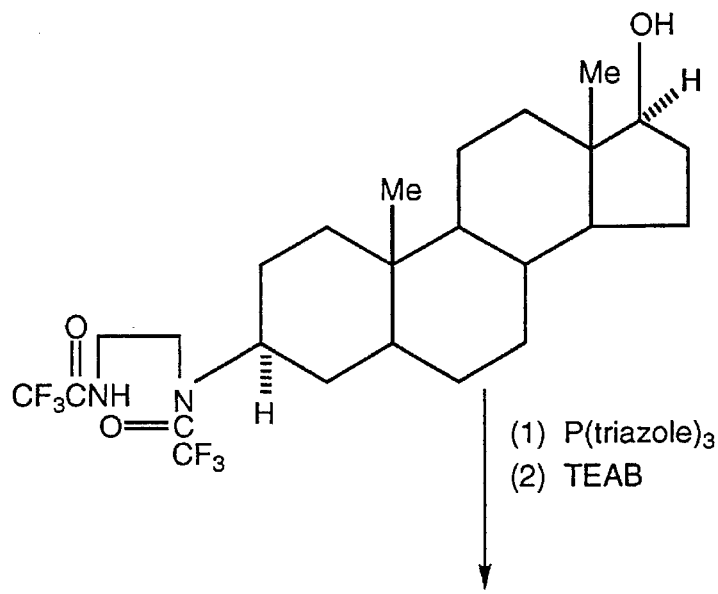
Figure 2:
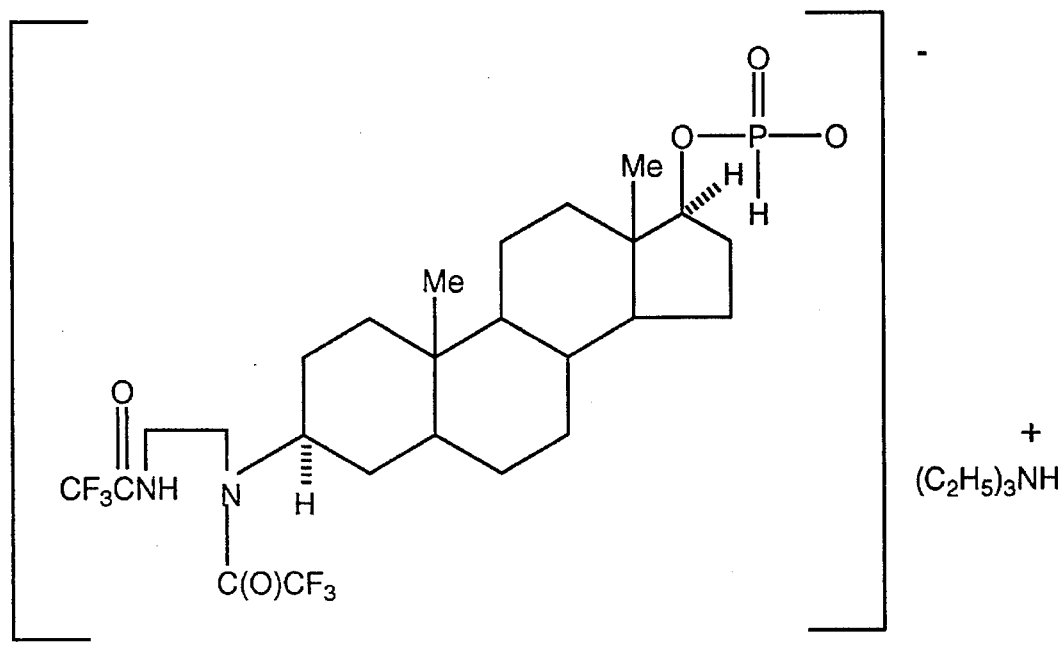

The reaction scheme used to prepare compound 4a is shown in FIG. 6. Briefly, the reaction scheme first involved the preparation of 3β-[N-(2-aminoethyl)-amino]-17β-hydroxy- 5α-androstane by the reductive amination of the 3-keto group on 17β-hydroxy-5α-androstan-3-one. The amines on 3β-[N-(2-aminoethyl)-amino]-17β-hydroxy-5α-androstane were protected by trifluoroacetylation resulting in the formation of 3β-[N-(2-N-trifluoroacylaminoethyl)-Ntrifluoroacylamino] -17β-hydroxy-5α-androstane. The third step involved the formation of compound 4a.

6.4.1. 3β-[N-(2-AMINOETHYL) -AMINO]-17β-HYDROXY-5α-ANDROSTANE

17β-Hydroxy-5α-androstan-3-one (403 mg, 1.39 mmol)(Aldrich Chemical Company) was added to a stirred solution of 0.745 mL 1,2-ethylenediamine (11.1 mmol) and 1.44 mL acetic acid (25.2 mmol) in 16.0 mL dry methanol (MeOH), followed by 104 mg (1.65 mmol, 1.19 equiv.) of sodium cyanoborohydride. After stirring at room temperature for 15 h, the reaction concentrated under reduced pressure. The residue was partitioned between methylene chloride and aqueous 1N sodium hydroxide, shaken, and separated. The organic layer was washed with water, dried over sodium sulfate, filtered, and concentrated under reduced pressure. The product was used without further purification.

6.4.2. 3β-[N-(2-N-TRIFLUOROACYLAMINOETHYL)-N-TRIFLUOROACYLAMINO] -17β-HYDROXY-5α-ANDROSTANE

Triethylamine (TEA) (3.0 mL, 21.5 mmol, 15.5 equiv.) was added to 1.39 mmol of crude 3β-[N-(2-aminoethyl)-amino]- 17β-hydroxy-5α-androstane in 8.0 mL dry methanol, followed by 3.21 mL (27.0 mmol, 19.4 equiv.) of ethyl trifluoroacetate (Aldrich). After stirring for 22 h at room temperature, the reaction was concentrated on a rotary evaporator. The residue was partitioned between methylene chloride and aqueous 1N hydrogen chloride (HCl), shaken, and separated. The organic layer was washed with water, saturated aqueous sodium bicarbonate, water, dried over sodium sulfate, filtered, and concentrated under reduced pressure. The product was purified by flash chromatography on a 20 mm column using one column volume of methylene chloride, one column volume of 5% methanol in methylene chloride, and then one column volume of 10% methanol in methylene chloride, as eluants. Isolation and concentration of the product afforded 155 mg (21.2% yield over two steps from 17β-hydroxy-5α-androstan-3-one) of pure product.

6.4.3.
3β-[N-(2-N-TRIFLUOROACYLAMINOETHYL)-N-TRIFLUORO-ACYLAMINO]-5α-ANDROSTAN-3β-O-YL-HYDROGEN-PHOSPHONATE TRIETHYLAMMONIUM SALT (4a)

The procedure used to prepare compound 4a was basically the same as that used for the preparation of compound 1a except that 155 mg (0.294 mmol) of 3β-[N-(2-N-trifluoroacylaminoethyl)-N-trifluoroacylamino]- 17β-hydroxy-5α-androstane was used. After the TEAB workup, the organic layer was dried and concentrated. The residue was purified by flash chromatography on a 20 mm column using one column volume of 1% TEA in methylene chloride, then one column volume of 1% TEA and 5% MeOH in methylene chloride, and then 1% TEA and 10% MeOH in methylene chloride. The procedure afforded 73.8 mg (36.4% yield) of pure product.

6.5. PREPARATION OF 5-N-TRIFLUOROACYL-5-(20-N-TRIFLUORO-ACYLAMINO- 5α-PREGNAN-3β-N-YL)-AMINOPENTAN-1-O-YL-HYDROGEN-PHOSPHONATE TRIETHYLAMMONIUM SALT (5a)

Figure 7A:
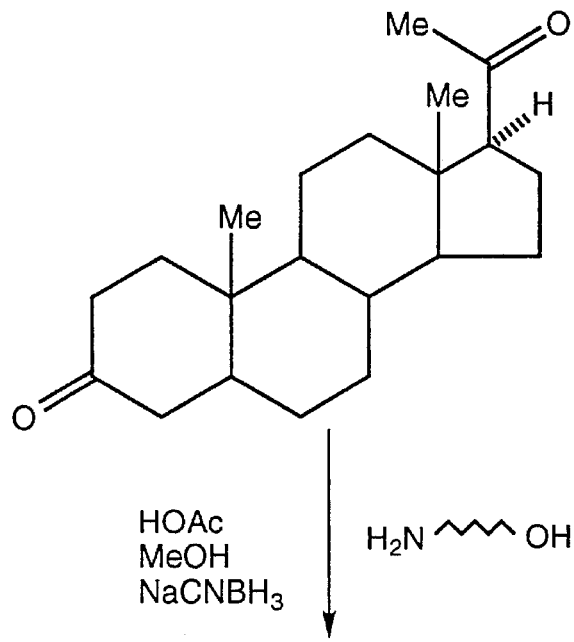
Figure 1:
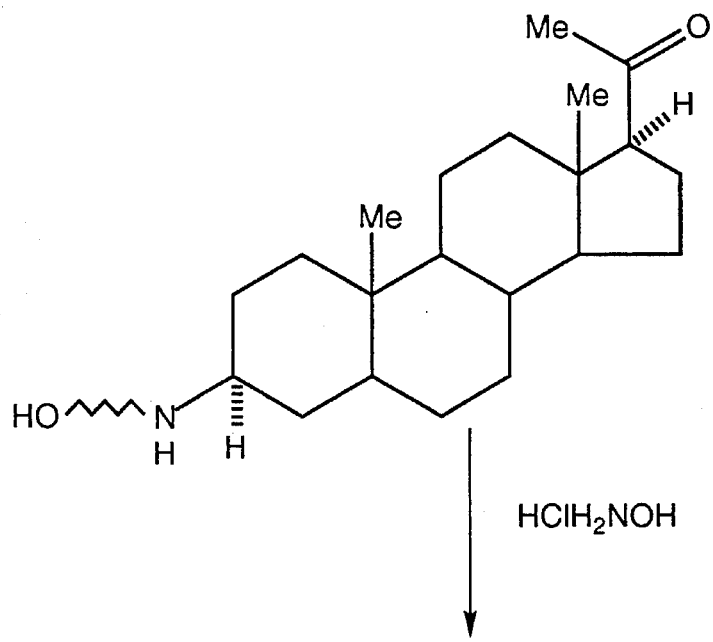
Figure 7A:
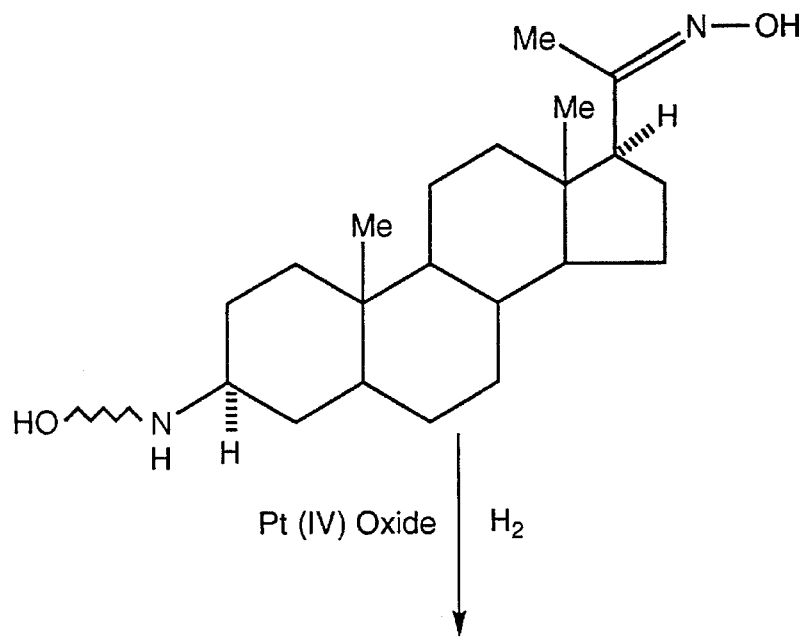
Figure 2:
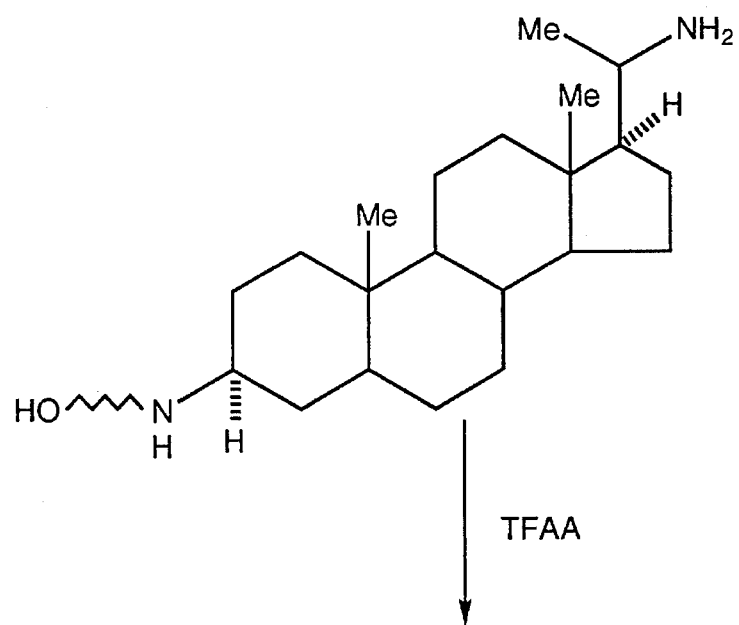
Figure 7A:
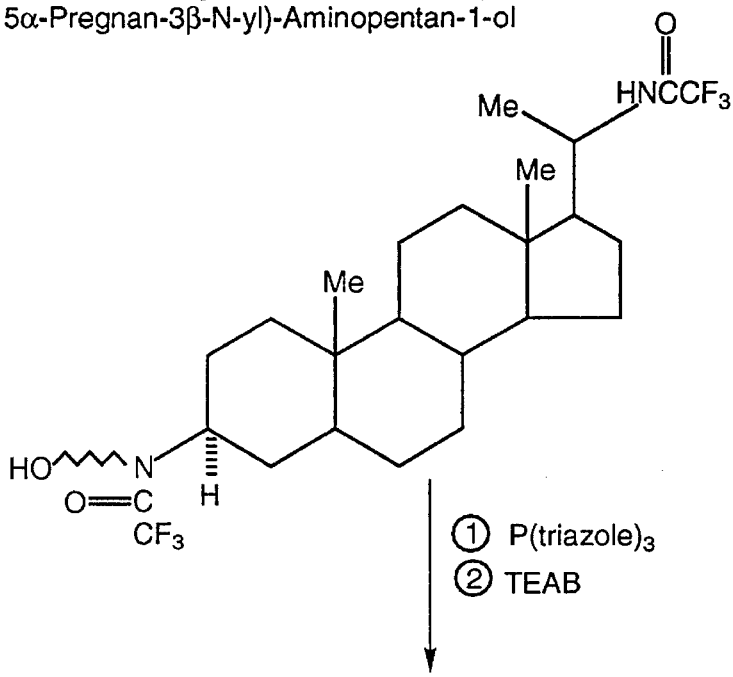
Figure 3:
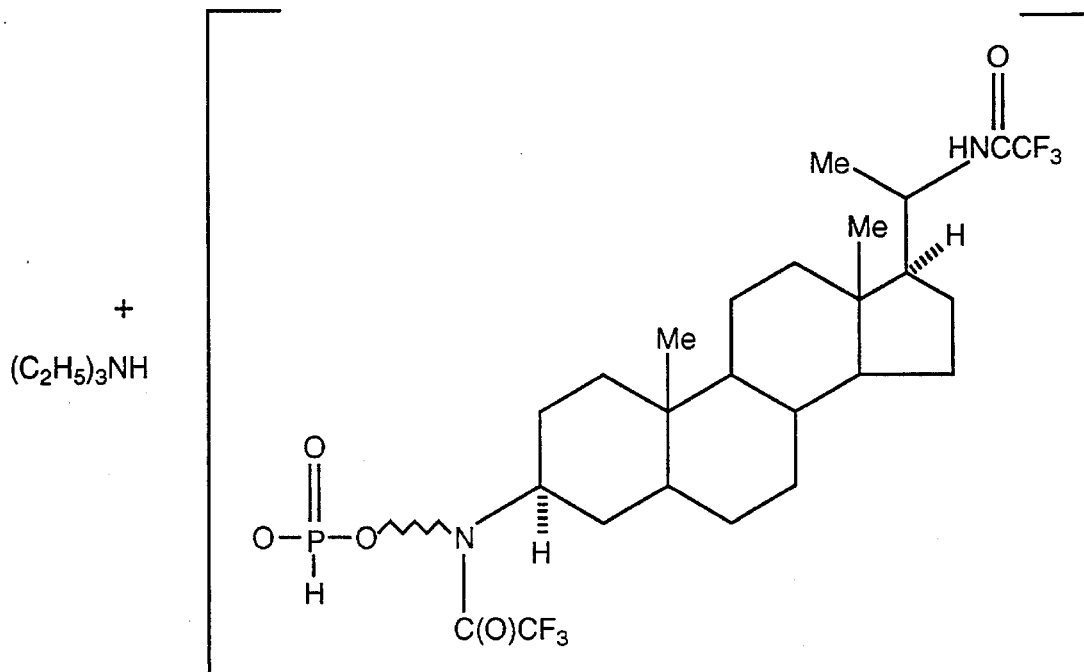
Figure 8A:
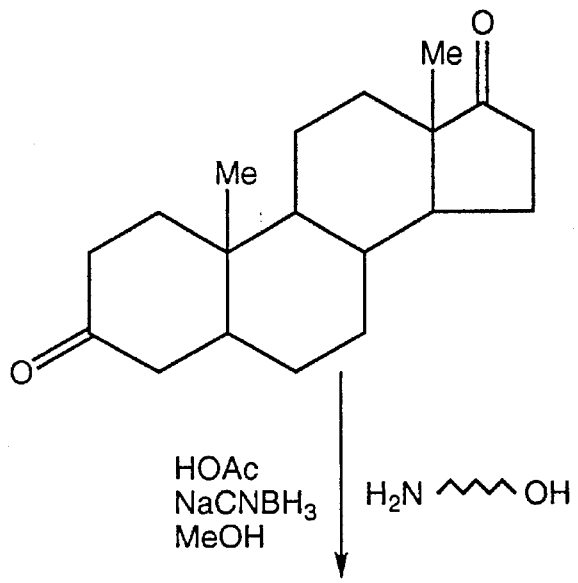
Figure 1:
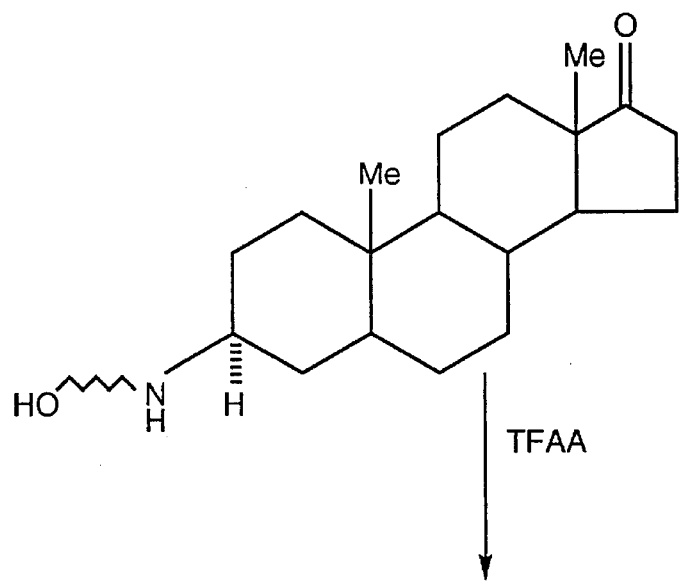
Figure 8A:
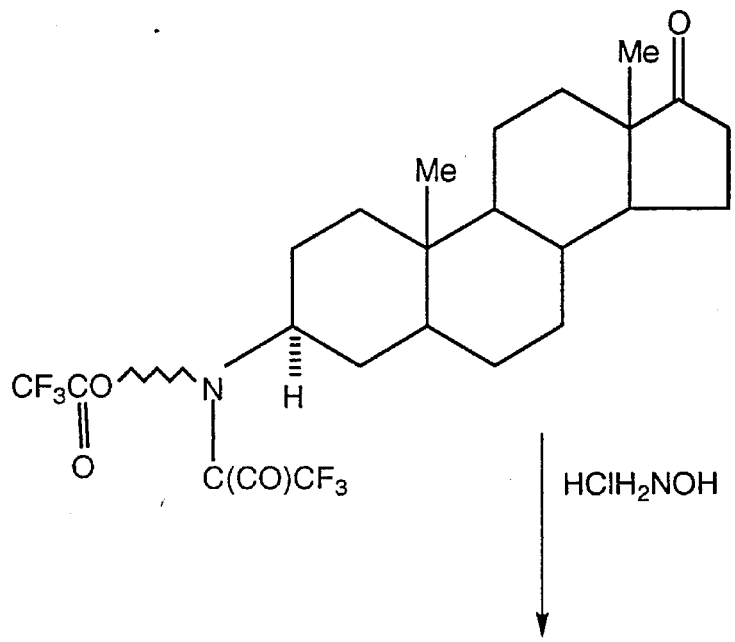
Figure 2:
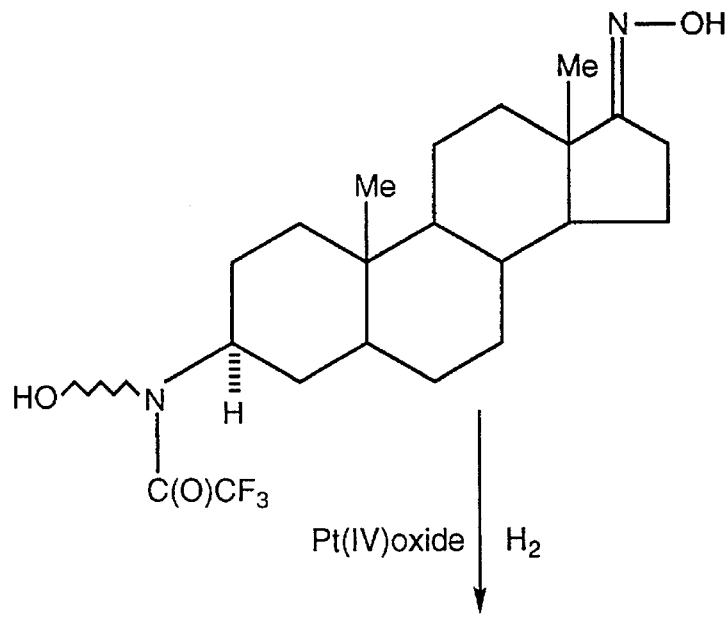
Figures 3, 8A:
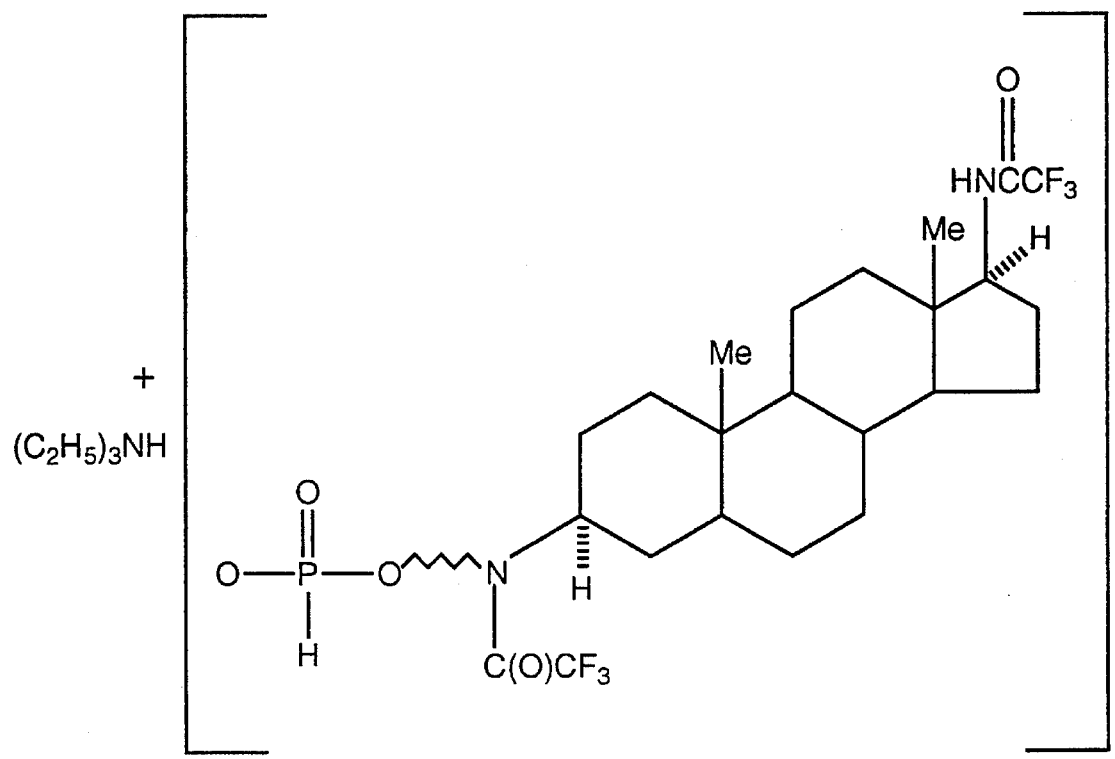
Figure 8A:
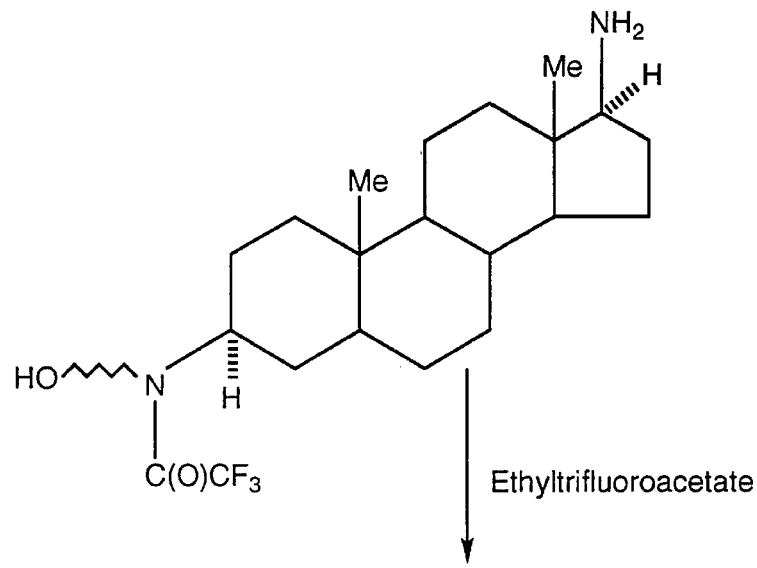

The reaction scheme used to prepare compound 5a is shown in FIG. 7. Briefly, the reaction scheme first involved the preparation of 5-(20-keto-5α-pregnan-3β-N-yl )-aminopentan- 1-ol by the reductive amination of the 3-keto group on 5α-pregnane-3,20-dione. The second step involved converting the 20-keto group into an oxime. In the third step, the oxime was reduced resulting in the formation of 5-(20-amino-5α-pregnan-3β-N-yl)-aminopentan-1-ol. The amines on 5-(20-amino-5α-pregnan-3β-N-yl)-aminopentan-1-ol were protected by trifluoroacetylation resulting in the formation of 5-N-trifluoroacyl-5-(20-N-trifluoroacylamino-5α-pregnan- 3β-N-yl)-aminopentan-1-ol. The fifth step involved the formation of compound 5a.

6.5.1.
5-(20-KETO-5α-PREGNAN-3β-N-YL)-AMINOPENTAN-1-OL

5α-Pregnane-3,20-dione (439 mg, 1.39 mmol) (Aldrich Chemical Company) was added to a stirred solution of 1.15 g 5-aminopentan-1-ol (11.1 mmol) and 0.720 mL acetic acid (12.6 mmol) in 16.0 mL dry methanol (MeOH), followed by 104 mg (1.65 mmol) of sodium cyanoborohydride. After stirring at room temperature for 15 h, the reaction mixture was concentrated under reduced pressure. The residue was partitioned between methylene chloride and aqueous 1N sodium hydroxide, shaken, and separated. The organic layer was washed with water, dried over sodium sul fate, filtered, and concentrated under reduced pressure. The product was used without further purification.

6.5.2.
5-(20-OXIMO-5α-PREGNAN-3β-N-YL)-AMINOPENTAN-1-OL 5-(20-Keto-5α-pregnan-3β-N-yl)-aminopentan-1-ol) (1.39 mmol) was first concentrated from dry pyridine and subsequently resuspended in 5.0 mL of dry pyridine. Hydroxylamine hydrochloride (600 mg, 8.63 mmol) was added to the 5-(20-keto-5α-pregnan-3β-N-yl)-aminopentan-1-ol solution. After stirring the reaction mixture for 16 h at room temperature, the reaction mixture was partitioned between methylene chloride and 1N aqueous sodium hydroxide, shaken, and separated. The aqueous layer was extracted with methylene chloride. The combined organic layers were washed with water, dried over sodium sulfate, filtered, and concentrated under reduced pressure. No further purification of the crude product was undertaken.

6.5.3.
5-(20-AMINO-5α-PREGNAN-3β-N-YL)-AMINOPENTAN-1-OL

A suspension of 300 mg of Pt(IV) oxide (Adams catalyst, from Aldrich) in 20 mL acetic acid was hydrogenated at 40 psi $H_2$ in a Parr reaction vessel with stirring at room temperature for 45 min. A solution of 1.39 mmol of crude 5-( 20-oximo-5α-pregnan-3β-N-yl)-aminopentan-1-ol in 5.0 mL acetic acid was added. The stirred mixture was hydrogenated at 40 psi of $H_2$ for 24 h at room temperature. The catalyst was removed by filtration through Celite. The filtrate was concentrated, and the residue was partitioned between methylene chloride and 1N aqueous sodium hydroxide, shaken, and separated. The aqueous layer was extracted with methylene chloride. The combined organic layers were washed with water, dried over sodium sulfate, filtered, and concentrated under reduced pressure. The crude product was taken on without further purification.

6.5.4.
5-N-TRIFLUOROACYL-5-(20-N-TRIFLUORO-ACYLAMINO-5α-PREGNAN-3β-N-YL)-AMINOPENTAN-1-OL

Trifluoroacetic anhydride (3.0 mL) was added dropwise to 1.39 mmol of crude 5-(20-amino-5α-pregnan-3β-N-yl)-aminopentan- 1-ol in 5 mL dry pyridine, which was first concentrated from dry pyridine. After stirring for 3.5 h at room temperature, the reaction mixture was partitioned between diethyl ether and aqueous 1N hydrogen chloride (HCl), shaken, and separated. The organic layer was washed successively with 1N HCl, water, saturated aqueous sodium bicarbonate, saturated aqueous NaCl, dried over sodium sulfate, filtered, and concentrated under reduced pressure. The residue was stirred in 15 mL of methanol for 8.5 h. The product was purified by flash chromatography on a 25 mm column using one column volume of methylene chloride, one column volume of 5% ethyl acetate in methylene chloride, and then one column volume of 10% ethyl acetate in methylene chloride, as eluants. Isolation and concentration of the product afforded 117 mg (14.1% yield over four steps) of product.

6.5.5.
5-N-TRIFLUOROACYL-5-(20-N-TRIFLUORO-ACYLAMINO-5α-PREGNAN-3β-N-YL)-AMINOPENTAN-1-O-YL-HYDROGEN PHOSPHONATE TRIETHYLAMMONIUM SALT (5a)

The procedure used to prepare compound 5a was basically the same as that used for the preparation of compound 1a except that 117 mg (0.196 mmol) of 5-N-trifluoroacyl-5-(20-N-trifluoroacylamino-5α-pregnan-3β-N-yl)-aminopentan-1-ol was used. After the TEAB workup, the organic layer was dried and concentrated. The residue was purified by flash chromatography on a 25 mm column using one column volume of 1% TEA in methylene chloride, then one column volume of 1% TEA and 5% MeOH in methylene chloride, and then 1% TEA and 10% MeOH in methylene chloride as eluants. The procedure afforded 88.0 mg (59.1% yield) of pure product.

6.6. PREPARATION OF 5-N-TRIFLUOROACYL-5-(17β-N-TRIFLUORO-ACYLAMINO-5α-ANDROSTAN-3β-N-YL)-AMINOPENTAN-1-O-YL-HYDROGEN-PHOSPHONATE TRIETHYLAMMONIUM SALT (6a)

The reaction scheme used to prepare compound 6a is shown in FIG. 8. Briefly, the reaction scheme first involved the preparation of 5-(17-keto-5α-androstan-3β-N-yl)-aminopentan-1-ol by the reductive amination of the 3-keto group on 5α-androstane-3,20-dione. The second step involved protecting the amine by trifluoroacetylation. The third step involved converting the 20-keto group into an oxime. In the fourth step, the oxime was reduced. The amine at the 20 position was subsequently protected by trifluoroacetylation resulting in the formation of 5-N-trifluoroacyl-5-(17β-N-trifluoroacylamino-5α-androstan-3β-N-yl)-aminopentan-1-ol. The fifth step involved the formation of compound 6a.

6.6.1. 5-(17-KETO-5α-ANDROSTAN-3β-N-YL)-AMINOPENTAN-1-OL

5α-androstane-3,17-dione (200 mg, 0.693 mmol) (Sigma Chemical Co.) was added to a stirred solution of 0.576 g 5-aminopentan-1-ol (5.59 mmol) and 0.320 mL acetic acid (5.59 mmol) in 8.0 mL dry methanol (MeOH), followed by 51.8 mg (0.825 mmol) of sodium cyanoborohydride. After stirring at room temperature for 16 h, the reaction mixture was concentrated under reduced pressure. The residue was partitioned between diethyl ether and aqueous 1N sodium hydroxide, shaken, and separated. The organic layer was washed with water, dried over sodium sulfate, filtered, and concentrated under reduced pressure. The product was used without further purification.

6.6.2. 5-N-TRIFLUOROACYL-5-(17-KETO-5α-ANDROSTAN-3β-N-YL)-AMINOPENTAN-1-YL-TRIFLUOROACETATE

Trifluoroacetic anhydride (0.320 mL) was added to 0.693 mmol of crude 5-(17-keto-5α-androstan-3β-N-yl)-aminopentan-1-ol in 3 mL dry diethyl ether and 1 mL dry pyridine. After 1 h, the reaction mixture was partitioned between diethyl ether and aqueous 1N hydrogen chloride (HCl), shaken, and separated. The organic layers were washed successively with water, saturated aqueous sodium bicarbonate, water, saturated aqueous NaCl, water, and dried over sodium sulfate, filtered, and concentrated under reduced pressure. The product was purified by flash chromatography on a 20 mm column using two column volumes of methylene chloride, and then 5% ethyl acetate in methylene chloride as eluants. Isolation of the product afforded 134 mg (34.1% yield over two steps) of pure product.

6.6.3. 5-N-TRIFLUOROACYL-5-(17-OXIMO-5α-ANDROSTAN-3β-N-YL)-AMINOPENTAN-1-OL

Hydroxylamine hydrochloride (151 mg, 2.19 mmol) was added to 134 mg (0.236 mmol) of 5-(N-trifluoroacyl-5-(17-keto-5α-androstan-3β-N-yl)-aminopentan-1-yl-trifluoroacetate in 0.639 mL of dry pyridine. After stirring the reaction mixture at room temperature for 21 h, the reaction mixture was partitioned between diethyl ether and saturated aqueous sodium bicarbonate, shaken, and separated. The organic layer was washed with saturated aqueous sodium bicarbonate, dried over sodium sulfate, filtered, and concentrated under reduced pressure. No further purification was undertaken of the crude product.

6.6.4. 5-N-TRIFLUOROACYL-5-(17β-AMINO-5α-ANDROSTAN-3β-N-YL)-AMINOPENTAN-1-OL

A suspension of 200 mg of Pt(IV) oxide (Adams catalyst, from Aldrich) in 20 mL acetic acid was hydrogenated at 40 psi $H_2$ in a Parr reaction vessel with stirring at room temperature for 45 min. A solution of 0.236 mmol of crude 5-N-trifluoroacyl-5-(17-oximo-5α-androstan-3β-N-yl)-aminopentan-1-ol in 5.0 mL acetic acid was added. The stirred mixture was hydrogenated at 40 psi of $H_2$ for 24 h at room temperature. The catalyst was removed by filtration through Celite. The filtrate was concentrated, and the residue was partitioned between methylene chloride and saturated aqueous sodium bicarbonate (the pH of the aqueous solution was kept at more than 8.5 by the addition of a small amount of 1N aqueous sodium hydroxide), shaken, and separated. The organic layer was washed with saturated aqueous bicarbonate, dried over sodium sulfate, filtered, and concentrated under reduced pressure. The crude product was taken on without further purification.

6.6.5. 5-N-TRIFLUOROACYL-5-(17β-N-TRIFLUORO-ACYLAMINO-5α-ANDROSTAN-3β-N-YL)-AMINOPENTAN-1-OL

TEA (0.239 mL, 1.71 mmol) and 0.256 mL (2.14 mmol) ethyl trifluoroacetate was added to 0.236 mmol of crude 5-N-trifluoroacyl-5-(17β-amino-5α-androstan-3β-N-yl)-aminopentan-1-ol in 0.9 mL dry methanol. After stirring for 2 h at room temperature, the reaction mixture was concentrated. The residue was partitioned between methylene chloride and aqueous 1N hydrogen chloride (HCl), shaken, and separated. The organic layer was washed successively with water, saturated aqueous sodium bicarbonate, and water and dried over sodium sulfate, filtered, and concentrated under reduced pressure. The product was purified by flash chromatography on a 20 mm column using one column volume of methylene chloride, one column volume of 5% methanol in methylene chloride, and then one column volume of 10% methanol in methylene chloride, as eluants. Isolation of the product afforded 53.0 mg (39.6 % yield over three steps) of pure product.

6.6.6. 5-N-TRIFLUOROACYL-5-(17β-N-TRIFLUORO-ACYLAMINO-5α-ANDROSTAN-3β-N-YL)-AMINOPENTAN-1-O-YL-HYDROGEN-PHOSPHONATE TRIETHYLAMMONIUM SALT (6a)

The procedure used to prepare compound 6a was basically the same as that used for the preparation of compound 1a except that 48 mg (0.0844 mmol) of 5-N-trifluoroacyl-5-(17β-N-trifluoroacylamino-5α-androstan-3β-N-yl)-aminopentan-1-ol was used. After the TEAB workup, the organic layer was dried and concentrated. The residue was purified by flash chromatography on a 20 mm column using one column volume of 1% TEA in methylene chloride, then one column volume of 1% TEA and 5% MeOH in methylene chloride, then one column volume of 1% TEA and 7.5% MeOH in methylene chloride and then 1% TEA and 15% MeOH in methylene chloride as eluants. This procedure afforded 23.9 mg (38.6% yield) of pure product.

6.7. INTRODUCTION OF THE STEROID AMINES INTO OLIGONUCLEOTIDES

The protected steroid amines were suspended in acetonitrile/pyridine and were introduced at the 5'-position of the oligonucleotides using the hydrogen-phosphonate method of Froehler et al. (1986, Nucl. Acids Res. 14: 5399–5407). The oligonucleotide sequence 5'-TCTCCCTCTCTTTT-3' was synthesized on a Biosearch machine using hydrogen-phosphonate chemistry. The oligonucleotide-steroid amine conjugates were fully deprotected by treatment with concentrated aqueous ammonia at 45° C. for 18 h.

The oligonucleotide-steroid amine conjugates were purified by 20% acrylamide/7M urea preparative gel electrophoresis. Gels were visualized by UV shadowing. Appropriate bands were cut out, crushed, and shaken with 3 mL 1X TBE buffer (0.089 M Tris base, 0.089 M boric acid, 2 mmol EDTA) at 37.5° C. for 15 h. The oligonucleotides were desalted on Fisher PrepSep C8 extraction columns with 2.0 mL water. The oligonucleotides were eluted from the C8 columns with 30% acetonitrile in water.

7. THERMAL MELTING OF COMPLEXES FORMED BETWEEN OLIGONUCLEOTIDE-STEROID AMINE CONJUGATES AND COMPLEMENTARY OLIGONUCLEOTIDES

Oligonucleotide conjugates 1–6 shown in FIG. 1, as well as the unconjugated oligonucleotide hereinafter referred to as the control, were individually mixed with an equivalent number of moles of a complementary oligonucleotide strand 14 nucleotides in length, 5'-AAAAGAGAGGGAGA-3', and then concentrated under reduced pressure. The oligonucleotides were reconstituted in 0.3 mL phosphate buffer (150 mM NaCl, 10 mM $Na_2HPO_4$, pH 7.1). Melting temperatures (Tm's) were recorded on a Gilford Response II temperature programmable UV spectrophotometer. Absorbances were read at 260 nm at 0.5° C. intervals. The temperature was increased from either 20° C.–75° C. or 20° C.–80° C. at the rate of 0.5° C./min. After the maximum temperature was reached, the Tm's were obtained from the maximum of the calculated first derivative of each Tm curve. The results are shown in Table I below.

TABLE I

Tm's OF OLIGONUCLEOTIDE-STEROID AMINE CONJUGATES

| Compound | Tm (°C.) |
| --- | --- |
| 1 | 52.5 |
| 2 | 54.5 |
| 3 | 54.5 |
| 4 | 52.0 |
| 5 | 51.25 |
| 6 | 51.75 |
| control | 50.75 |

All of the oligonucleotide-steroid amine conjugates showed an increased Tm compared to the control oligonucleotide. These results indicate that the oligonucleotide-steroid amine conjugates form more stable complexes with complementary DNA sequences than the unconjugated oligonucleotide alone.

Oligonucleotide-steroid amine conjugate 6 was also separately mixed with an equivalent number of moles of a complementary 14 mer RNA strand that was prepared from a DNA template using T7 RNA polymerase (Milligan et al., 1987, Nucl. Acids Res. 15: 8783–8788). After concentrating the mixture under reduced pressure, the DNA-RNA complex was reconstituted in 0.3 mL Tris buffer (100 mM NaCl, 50 mM Tris-base, pH 7.5). Tm's were determined as described in the previous paragraph above. The Tm of the control oligodeoxyribonucleotide+RNA complement was 59.5° C. and the Tm of the oligonucleotide-steroid amine conjugate 6 was 61° C. These results indicate that an oligonucleotide-steroid amine conjugate forms a more stable complex with RNA than the unconjugated oligonucleotide.

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An oligonucleotide conjugate comprising an oligonucleotide containing from about 2 to about 30 nucleotides or analog thereof conjugated to a molecule at a terminal 2', 3' or 5' position of the oligonucleotide, which molecule comprises a rigid structure consisting of:

(a) a cyclic ring portion containing from about 2 to about 6 n-membered rings where n=4–8;

(b) a first terminal amine wherein said amine is directly attached to, or is attached to a carbon atom that is directly attached to said cyclic ring portion; and (c) a second terminal group consisting of a phosphate, a second amine or a cationic sulphur wherein said second terminal group is contained within, is directly attached to, or is attached to an atom that is directly attached to said cyclic ring portion or the first terminal amine;

wherein said cyclic ring portion may be a substituted derivative thereof having methyl or lower alkyl groups at any position other than those positions attaching said first terminal amine and containing or attaching said second terminal group.

2. The oligonucleotide conjugate of claim 1 in which the oligonucleotide is an oligodeoxyribonucleotide.

3. The oligonucleotide conjugate of claim 1 in which the sequence of the oligonucleotide is selected from the group consisting of a single stranded nucleic acid sequence, a double stranded nucleic acid sequence, a cellular nucleic acid sequence and a viral nucleic acid sequence.

4. The oligonucleotide conjugate of claim 3 in which the sequence of the oligonucleotide is selected from the group consisting of RNA and DNA.

5. The oligonucleotide conjugate of claim 1 in which the analog is selected from the group consisting of a modified base, a modified sugar moiety, modified phosphate backbone and an α-anomeric oligonucleotide.

6. The oligonucleotide conjugate of claim 5 in which the modified base is selected from the group consisting of 5-fluorouracil, 5-bromouracil, 5-chlorouracil, 5-iodouracil, xanthine, 4-acetylcytosine, 5-(carboxyhydroxyl-methyl) uracil, 5-carboxymethylaminomethyl-2-thiouridine, 5-carboxymethyl-aminomethyluracil, inosine, N6-isopentenyladenine, 2-methyladenine, 2-methyl-guanine, 5-methylcytosine, N6-adenine, 5-methylaminomethyluracil, 5-methoxyamino-methyl-2-thiouracil, 5-methoxycarboxymethyluracil, 5-methoxyuracil, 2-methylthio-N6-isopentenyladenine, uracil-5-oxyacetic acid, pseudouracil, 2-thiocytosine, 5-methyl-2-thiouracil, 2-thiouracil, 4-thiouracil, 5-methyluracil, uracil-5-oxyacetic acid methylester, uracil-5-oxyacetic acid, 3-(3-amino-3-N-2-carboxypropyl) uracil, and 2,6-diaminopurine.

7. The oligonucleotide conjugate of claim 5 in which the modified sugar moiety is selected from the group consisting of arabinose, xylulose, and hexose.

8. The oligonucleotide conjugate of claim 5 in which the modified phosphate backbone is selected from the group consisting of a phosphorothioate, a phosphorodithioate, a phosphoramidothioate, a phosphoramidate, a phosphordiamidate, a methylphosphonate, an alkyl phosphotriester, and a formacetal.

9. The oligonucleotide conjugate of claim 1 in which the structure is a non-aromatic cyclic compound or substituted derivative thereof.

10. The oligonucleotide conjugate of claim 9 in which the non-aromatic cyclic compound is selected from the group consisting of a monocyclic, a polycyclic, and a fused polycyclic.

11. The oligonucleotide conjugate of claim 1 in which the molecule is a steroid or substituted derivative thereof.

12. The oligonucleotide conjugate of claim 11 in which the steroid is selected from the group consisting of androstane, pregnane, pregnene, cholesterol, dexamethasone, estradiol, progesterone, pregnelone, corticosteroid, and testosterone.

13. The oligonucleotide conjugate of claim 12 in which the steroid is selected from the group consisting of androstane and pregnane.

14. The oligonucleotide conjugate of claim 1 in which the first amine is selected from the group consisting of a substituted cyclic amine, and a substituted quaternary amine.

15. The oligonucleotide conjugate of claim 1 in which the first amine is directly attached to the structure or is attached to a carbon that is directly attached to the structure.

16. The oligonucleotide conjugate of claim 12 in which the first amine is attached to the 3-position of the androstane or the 3-position of the pregnane.

17. The oligonucleotide conjugate of claim 12 in which the first amine is attached to the 17-position of the androstane or to the 20-position of the pregnane.

18. The oligonucleotide conjugate of claim 12 in which the first amine is attached to the 3-position and the 17-position of the androstane or the first amine is attached to the 3-position and the 20-position of the pregnane.

19. The oligonucleotide conjugate of claim 17 in which the amine at the 3-position and the amine at the 17-position of the androstane are cis to one another.

20. The oligonucleotide conjugate of claim 14 in which the substituents on the quaternary amine are selected from the group consisting of hydrogen, alkyl, cycloalkyl, aryl, alkaryl, hydroxy, a cyclic amine, a quaternary amine, and substituted derivatives thereof.

21. The oligonucleotide conjugate of claim 14 in which the substituents on the cyclic amine are selected from the group consisting of hydrogen, alkyl, cycloalkyl, aryl, alkaryl, hydroxy, a cyclic amine, a quaternary amine, and substituted derivatives thereof.

22. The oligonucleotide conjugate of claim 14 in which the first amine is an amine having the formula $R_1NR_2$ in which $R_1$ and $R_2$ are selected from the group consisting of hydrogen, alkyl, cycloalkyl, aryl, alkaryl, hydroxy, a cyclic amine, a quaternary amine, and substituted derivatives thereof.

23. The oligonucleotide conjugate of claim 11 in which the steroid or substituted derivative is conjugated to at least one base moiety of the oligonucleotide.

24. The oligonucleotide conjugate of claim 23 in which the oligonucleotide is conjugated to the steroid or substituted derivative through a linking chain.

25. The oligonucleotide conjugate of claim 24 in which the linking chain comprises an aliphatic alkyl or branched aliphatic alkyl, or aromatic or substituted derivative thereof, or a heteroatom containing an alkyl or branched chain or aromatic or substituted derivative thereof of about 1 to about 20 carbon atoms.

26. The oligonucleotide conjugate of claim 11 in which the steroid or substituted derivative is conjugated to at least one sugar moiety of the oligonucleotide.

27. The oligonucleotide conjugate of claim 11 in which the steroid or substituted derivative is conjugated to at least one phosphate moiety of the oligonucleotide.

28. The oligonucleotide conjugate of claim 23 or 26 or 27 which the oligonucleotide is conjugated to the steroid or substituted derivative through a linking chain.

29. The oligonucleotide conjugate of claim 28 in which the linking chain comprises an aliphatic alkyl or branched aliphatic alkyl or aromatic or substituted derivatives thereof, or a heteroatom containing an alkyl or branched chain or aromatic or substituted derivative thereof, of about 1 to 20 carbon atoms.

30. The oligonucleotide conjugate of claim 1 or 11 in which the oligonucleotide or analog consists of at least 8 nucleotides.

31. An oligonucleotide conjugate comprising an oligonucleotide containing from about 2 to about 30 nucleotides or analog thereof, which oligonucleotide or analog (a) consists of at least 8 nucleotides; and (b) is conjugated to a molecule at a terminal 2', 3' or 5' position of the oligonucleotide, which molecule comprises a rigid structure consisting of:

(a) a cyclic ring portion containing from about 2 to about 6 n-membered rings where n=4–8;

(b) a first terminal amine wherein said amine is directly attached to, or is attached to a carbon atom that is directly attached to said cyclic ring portion; and (c) a second terminal group consisting of a phosphate, a second amine or a cationic sulphur wherein said second terminal group is contained within, is directly attached to, or is attached to an atom that is directly attached to said cyclic ring portion or the first terminal amine;

wherein said cyclic ring portion may be a substituted derivative having methyl or lower alkyl groups at any position other than those positions attaching said first terminal amine and containing or attaching said second terminal group.

32. An oligonucleotide conjugate comprising an oligonucleotide containing from about 2 to about 30 nucleotides or analog thereof conjugated to a molecule at a terminal 2', 3' or 5' position of the oligonucleotide, wherein said molecule has the structure

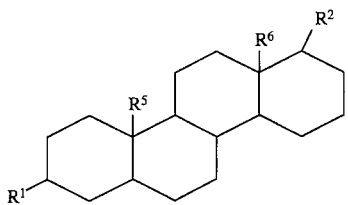
wherein:
R¹ is $OPO_3^=$, $NH_2$ or $NHR^3$;
R² is $OPO_3^=$, $NH_2$, $NHR^3$, $R^4OPO_3^=$, $R^4NH_2$ or $R^4NHR^3$;
R³ is $(CH_2)_2NH_2$, $(CH_2)_5$ or $(CH_2)_4CH_3$;
R⁴ is a straight or branch chained alkyl group having 1 to 4 carbon atoms;
R⁵ is hydrogen or methyl; and
R⁶ is hydrogen or methyl;
wherein said oligonucleotide or analog thereof is conjugated to said molecule at R¹ or R².
* * * * *